(12) United States Patent
Harari et al.

(10) Patent No.: US 10,792,029 B2
(45) Date of Patent: Oct. 6, 2020

(54) PADDED TRANSOSSEOUS SUTURE

(71) Applicant: MININVASIVE LTD., Magal (IL)

(72) Inventors: Boaz Harari, Haifa (IL); Mordehai Sholev, Amikam (IL); Ronen Raz, Magal (IL); Arnon Mousaiuf, Atlit (IL); Dror Rosner, Holon (IL); Paul Mraz, Duxbury, MA (US)

(73) Assignee: MININVASIVE LTD., Magal (IL)

( * ) Notice: Subject to any disclaimer, the term of this patent is extended or adjusted under 35 U.S.C. 154(b) by 8 days.

(21) Appl. No.: 15/509,066

(22) PCT Filed: Sep. 9, 2015

(86) PCT No.: PCT/IL2015/050923
§ 371 (c)(1),
(2) Date: Mar. 6, 2017

(87) PCT Pub. No.: WO2016/038614
PCT Pub. Date: Mar. 17, 2016

(65) Prior Publication Data
US 2017/0252031 A1  Sep. 7, 2017

Related U.S. Application Data

(60) Provisional application No. 62/047,674, filed on Sep. 9, 2014.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/042* (2013.01);
(Continued)

(58) Field of Classification Search
CPC ........ A61B 17/0401; A61B 2017/0409; A61B 2017/0403; A61B 2017/0406;
(Continued)

(56) References Cited

U.S. PATENT DOCUMENTS 2,579,192 A    12/1951   Kohl
5,250,055 A    10/1993   Moore et al.
(Continued)

FOREIGN PATENT DOCUMENTS

CN          101193600      9/2010
EP           1898812        3/2008
(Continued)

OTHER PUBLICATIONS

An Office Action dated May 8, 2018, which issued during the prosecution of U.S. Appl. No. 15/665,838.
(Continued)

*Primary Examiner* — Christopher L Templeton
*Assistant Examiner* — Andrew P. Restaino
(74) *Attorney, Agent, or Firm* — Sughrue Mion, PLLC

(57) ABSTRACT

A bone suture assembly including a flexible generally cylindrical sleeve, a plurality of lengths of suture extending through the generally cylindrical sleeve, and at least one sleeve securing thread associated with the generally cylindrical sleeve. A bone suture retaining method including engaging a suture with a bone engaging sleeve, inserting the suture and the bone engaging sleeve engaged thereby into a transosseous tunnel formed into a bone by pulling the bone engaging sleeve into the transosseous tunnel and retaining the suture and the bone engaging sleeve in the transosseous tunnel by virtue of the bone engaging sleeve being unable to fit through an aperture in the bone.

8 Claims, 48 Drawing Sheets

(52) U.S. Cl.
CPC .............. *A61B 2017/0403* (2013.01); *A61B 2017/0406* (2013.01); *A61B 2017/0437* (2013.01); *A61B 2017/0445* (2013.01); *A61B 2017/0458* (2013.01); *A61B 2017/0495* (2013.01); *A61F 2/0805* (2013.01); *A61F 2002/0835* (2013.01); *A61F 2002/0882* (2013.01); *A61F 2002/0888* (2013.01)

(58) Field of Classification Search
CPC ...... A61B 2017/042; A61B 2017/0437; A61B 2017/0445; A61B 2017/0458; A61B 2017/0495; A61F 2002/0835; A61F 2002/0882; A61F 2002/0888; A61F 2/0805; A61F 2/0811
USPC ........................................................ 606/232
See application file for complete search history.

(56) References Cited

U.S. PATENT DOCUMENTS

| | | | |
|---|---|---|---|
| 5,387,221 A | | 2/1995 | Bisgaard |
| 5,499,991 A | | 3/1996 | Garman et al. |
| 5,656,605 A | * | 8/1997 | Hansson ............ A61B 17/1128 424/422 |
| 5,665,096 A | | 9/1997 | Yoon |
| 5,681,333 A | | 10/1997 | Burkhart et al. |
| 5,961,530 A | | 10/1999 | Moore |
| 6,328,744 B1 | | 12/2001 | Harari |
| 6,443,963 B1 | | 9/2002 | Baldwin |
| 6,523,417 B1 | | 2/2003 | Donahue |
| 7,029,479 B2 | | 4/2006 | Tallarida |
| 7,097,648 B1 | | 8/2006 | Globerman et al. |
| 7,166,116 B2 | | 1/2007 | Lizardi et al. |
| 7,494,496 B2 | * | 2/2009 | Swain ................ A61B 17/0401 606/151 |
| 7,662,171 B2 | | 2/2010 | West et al. |
| 8,088,130 B2 | | 1/2012 | Kaiser et al. |
| 8,282,643 B2 | | 10/2012 | Dross |
| 8,282,657 B2 | | 10/2012 | McClurg et al. |
| 9,763,659 B2 | | 9/2017 | Sholev et al. |
| 2002/0040227 A1 | | 4/2002 | Harari |
| 2003/0078599 A1 | | 4/2003 | O'Quinn |
| 2006/0195121 A1 | | 8/2006 | Chu |
| 2006/0271060 A1 | | 11/2006 | Gordon |
| 2007/0005067 A1 | | 1/2007 | Dross |
| 2007/0179509 A1 | | 8/2007 | Nagata et al. |
| 2008/0109015 A1 | | 5/2008 | Chu et al. |
| 2008/0228224 A1 | | 9/2008 | Sauer |
| 2009/0012538 A1 | | 1/2009 | Saliman et al. |
| 2009/0062819 A1 | | 3/2009 | Burkhart |
| 2009/0069823 A1 | | 3/2009 | Foerster |
| 2009/0105729 A1 | | 4/2009 | Zentgraf |
| 2009/0105743 A1 | | 4/2009 | Chu |
| 2009/0131956 A1 | | 5/2009 | Dewey |
| 2009/0138029 A1 | | 5/2009 | Saliman et al. |
| 2009/0157076 A1 | | 6/2009 | Athas et al. |
| 2009/0206128 A1 | | 8/2009 | Hueil et al. |
| 2009/0270862 A1 | | 10/2009 | Arcenio |
| 2009/0312782 A1 | | 12/2009 | Park |
| 2010/0076436 A1 | | 3/2010 | Hajianpour |
| 2010/0106194 A1 | | 4/2010 | Bonutti et al. |
| 2010/0152751 A1 | | 6/2010 | Meade et al. |
| 2010/0191248 A1 | | 7/2010 | Mehta et al. |
| 2010/0198258 A1 | | 8/2010 | Heaven et al. |
| 2010/0318139 A1 | | 12/2010 | Beauchamp |
| 2011/0022063 A1 | | 1/2011 | McClurg |
| 2011/0098727 A1 | * | 4/2011 | Kaiser ................ A61B 17/0401 606/144 |
| 2011/0106124 A1 | | 5/2011 | Beauchamp |
| 2011/0301577 A1 | | 12/2011 | Simmen et al. |
| 2012/0239085 A1 | * | 9/2012 | Schlotterback ........ A61B 17/04 606/228 |
| 2012/0323248 A1 | | 12/2012 | Dross |
| 2013/0123810 A1 | | 5/2013 | Brown et al. |
| 2013/0144337 A1 | | 6/2013 | Stone et al. |
| 2013/0144338 A1 | * | 6/2013 | Stone ................ A61B 17/0401 606/232 |
| 2013/0178854 A1 | | 7/2013 | Sholev et al. |
| 2013/0296931 A1 | | 11/2013 | Sengun |
| 2014/0214038 A1 | | 7/2014 | Sholev |
| 2014/0219483 A1 | | 8/2014 | Hong |
| 2014/0249577 A1 | * | 9/2014 | Pilgeram ............ A61B 17/0485 606/228 |
| 2014/0303625 A1 | | 10/2014 | Sholev |
| 2015/0045795 A1 | | 2/2015 | Sholev et al. |
| 2015/0173754 A1 | * | 6/2015 | Norton ............. A61B 17/06166 606/228 |
| 2015/0258332 A1 | | 9/2015 | Bentley et al. |
| 2015/0351743 A1 | | 12/2015 | Stiggelbout |
| 2015/0351759 A1 | | 12/2015 | Bennett et al. |
| 2016/0015380 A1 | | 1/2016 | Sholev et al. |

FOREIGN PATENT DOCUMENTS

| | | |
|---|---|---|
| EP | 1970016 | 9/2008 |
| EP | 2698128 | 2/2014 |
| EP | 2698128 B1 * | 7/2017 |
| GB | 2154484 | 9/1985 |
| JP | 1996-033635 | 2/1996 |
| JP | 1996-509918 | 10/1996 |
| JP | H10-52431 | 2/1998 |
| JP | 2003-501132 | 1/2003 |
| JP | 2008-510526 | 4/2008 |
| JP | 2008-546489 | 12/2008 |
| JP | 5474996 | 4/2014 |
| WO | 96/27331 | 9/1996 |
| WO | 97/47246 | 12/1997 |
| WO | 2000/74578 | 12/2000 |
| WO | 2002/007609 | 1/2002 |
| WO | 2009/107121 | 9/2009 |
| WO | 10/056785 | 5/2010 |
| WO | 10/056786 | 5/2010 |
| WO | 10/056787 | 5/2010 |
| WO | 2011/160166 | 12/2011 |
| WO | 2012/007941 | 1/2012 |
| WO | 2013/027209 | 2/2013 |
| WO | 2013/027210 | 2/2013 |
| WO | 2013/071234 | 5/2013 |
| WO | 2013/102909 | 7/2013 |
| WO | 2014/147619 | 9/2014 |
| WO | 2016/038614 | 3/2016 |
| WO | 2017/051404 | 3/2017 |
| WO | 2017/115355 | 7/2017 |

OTHER PUBLICATIONS

An International Search Report and a Written Opinion both dated May 24, 2018, which issued during the prosecution of Applicant's PCT/IL2018/050180.
Provisional U.S. Appl. No. 61/636,751, filed Apr. 23, 2012.
Provisional U.S. Appl. No. 61/584,267, filed Jan. 8, 2012.
Provisional U.S. Appl. No. 61/526,717, filed Aug. 24, 2011.
Provisional U.S. Appl. No. 61/363,247, filed Jul. 11, 2010.
Provisional U.S. Appl. No. 61/714,813, filed Oct. 17, 2012.
An International Search Report and a Written Opinion both dated Jan. 23, 2013, which issued during the prosecution of Applicant's PCT/IL2012/000318.
An International Search Report and a Written Opinion both dated Dec. 5, 2011, which issued during the prosecution of Applicant's PCT/IL2011/000549.
An International Search Report and a Written Opinion both dated May 10, 2013 which issued during the prosecution of Applicant's PCT/IL2013/050030.
An International Search Report dated Jan. 8, 2013 which issued during the prosecution of Applicant's PCT/IL2012/000319.
An English translation of an Office Action dated Mar. 24, 2015, which issued during the prosectuion of Japanese Patent Application No. 519213/2013.
An English translation of an Office Action dated Jul. 3, 2014 which issued during the prosecution of Chinese Patent Application 2011800437287.

(56) References Cited

OTHER PUBLICATIONS

An International Search Report and Written Opinion both dated Jul. 11, 2014, which issued during the prosecutuion of Applicant's PCT/IL 14/50299.
An International Preliminary Search Report dated Aug. 26, 2014, which issued during the prosecution of Applicant's PCT/IL2013/050030.
An International Preliminary Report dated Feb. 25, 2014 which issued during the prosecution of Applicant's PCT/IL2012/000319.
Written Opinion dated Jan. 8, 2013 which issued during the prosecution of Applicant's PCT/IL2012/000319.
An International Preliminary Report dated Feb. 25, 2014 which issued during the prosecution of Applicant's PCT/IL2012/000318.
An Office Action dated Apr. 5, 2014 which issued during the prosecution of Australian Patent Application No. 2011277949.
An Office Action dated Jul. 11, 2016 which issued during the prosecution of Australian Patent Application No. 2012298197.
An International Search Report and a Written Opinion both dated Jun. 9, 2016, which issued during the prosecution of Applicant's PCT/IL2015/050978.
An Office Action dated Jun. 27, 2016 which issued during the prosecution of Australian Patent Application No. 2015202032.
An Office Action dated May 24, 2016 which issued during the prosecution of Chinese Patent Application No. 2013800124154.
European Search Report dated Jun. 19, 2015 which issued during the prosecution of Applicant's European App No. 12826407.
European Search Report dated Jan. 27, 2016 which issued during the prosecution of Applicant's European App No. 13733888.
An Invitation to pay additional fees dated Dec. 23, 2015, which issued during the prosecution of Applicant's PCT/IL2015/050923.
Notice of Allowance dated Jan. 7, 2016, which issued during the prosecution of Japanese Patent Application No. 519213/2013.
An Office Action dated Feb. 25, 2016, which issued during the prosecution of U.S. Appl. No. 13/809,562.
An Office Action dated Sep. 1, 2016, which issued during the prosecution of U.S. Appl. No. 14/240,227.
An Invitation to pay additional fees dated Mar. 30, 2016, which issued during the prosecution of Applicant's PCT/IL2015/050978.
An English translation of an Office Action dated Oct. 13, 2015, which issued during the prosecution of Chinese Patent Application 2012800518842.
An English translation of an Office Action dated May 16, 2016, which issued during the prosecution of Chinese Patent Application 2012800518842.
Provisional U.S. Appl. No. 61/802,958, filed Mar. 18, 2013.
Provisional U.S. Appl. No. 61/887,561, filed Oct. 7, 2013.
An International Preliminary Report dated Sep. 22, 2016, which issued during the prosecution of Applicant's PCT/IL2014/050299.
Provisional U.S. Appl. No. 62/273,632, filed Dec. 31, 2015.
An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.
An International Search Report and a Written Opinion both dated Aug. 23, 2017, which issued during the prosecution of Applicant's PCT/IL2016/051379.
An English translation of an Office Action dated Sep. 6, 2016, which issued during the prosecution of Japanese Patent Application No. 526597/2014.
An Office Action dated Aug. 3, 2016, which issued during the prosecution of U.S. Appl. No. 14/240,082.
An English translation of an Office Action dated May 16, 2017, which issued during the prosecution of Japanese Patent Application No. 526597/2014.
An Office Action dated Nov. 22, 2016 which issued during the prosecution of Japanese Patent Application No. 550801/2014.
An Office Action dated Oct. 13, 2016, which issued during the prosecution of U.S. Appl. No. 14/240,082.
An Office Action dated Mar. 21, 2017, which issued during the prosecution of U.S. Appl. No. 14/240,227.
An Office Action dated Mar. 20, 2017, which issued during the prosecution of U.S. Appl. No. 14/240,082.
European Search Report dated May 11, 2017, which issued during the prosecution of Applicant's European App No. 11806391.6.
European Search Report dated Jan. 17, 2017, which issued during the prosecution of Applicant's European App No. 14769413.7.
Notice of Allowance dated May 26, 2017, which issued during the prosecution of U.S. Appl. No. 13/809,562.
An Office Action dated Apr. 6, 2017, which issued during the prosecution of U.S. Appl. No. 14/370,884.
An Office Action dated Jul. 13, 2017, which issued during the prosecution of U.S. Appl. No. 14/370,884.
An Office Action dated Dec. 2, 2016, which issued during the prosecution of U.S. Appl. No. 13/809,562.
An International Preliminary Report dated Mar. 26, 2013, which issued during the prosecution of Applicant's PCT/IL2011/000549.
An International Preliminary Report dated Mar. 14, 2017, which issued during the prosecution of Applicant's PCT/IL2015/050923.
Notice of Allowance dated Sep. 1, 2017, which issued during the prosecution of U.S. Appl. No. 14/240,082.
Notice of Allowance dated Aug. 11, 2017, which issued during the prosecution of U.S. Appl. No. 13/809,562.
Notice of Allowance dated May 26, 2017, which issued during the prosecution of U.S. Appl. No. 14/240,227.
An Office Action dated Jul. 5, 2017, which issued during the prosecution of Australian Patent Application No. 2013207071.
An Office Action dated Mar. 31, 2017, which issued during the prosecution of Canadian Patent Application No. 2804255.
An English translation of an Office Action dated Feb. 9, 2016, which issued during the prosecution of Israel Patent Application No. 224079.
An English translation of an Office Action dated May 31, 2017, which issued during the prosecution of Chinese Patent Application 201480016633.X.
Provisional U.S. Appl. No. 62/047,674, filed Sep. 9, 2014.
Notice of Allowance together with the English translation dated Nov. 1, 2017, which issued during the prosecution of Korean Patent Application No. 10-2013-7003093.
An Office Action dated Mar. 13, 2020, which issued during the prosecution of U.S. Appl. No. 15/760,496.
An Office Action dated Mar. 13, 2020, which issued during the prosecution of U.S. Appl. No. 16/066,171.

* cited by examiner

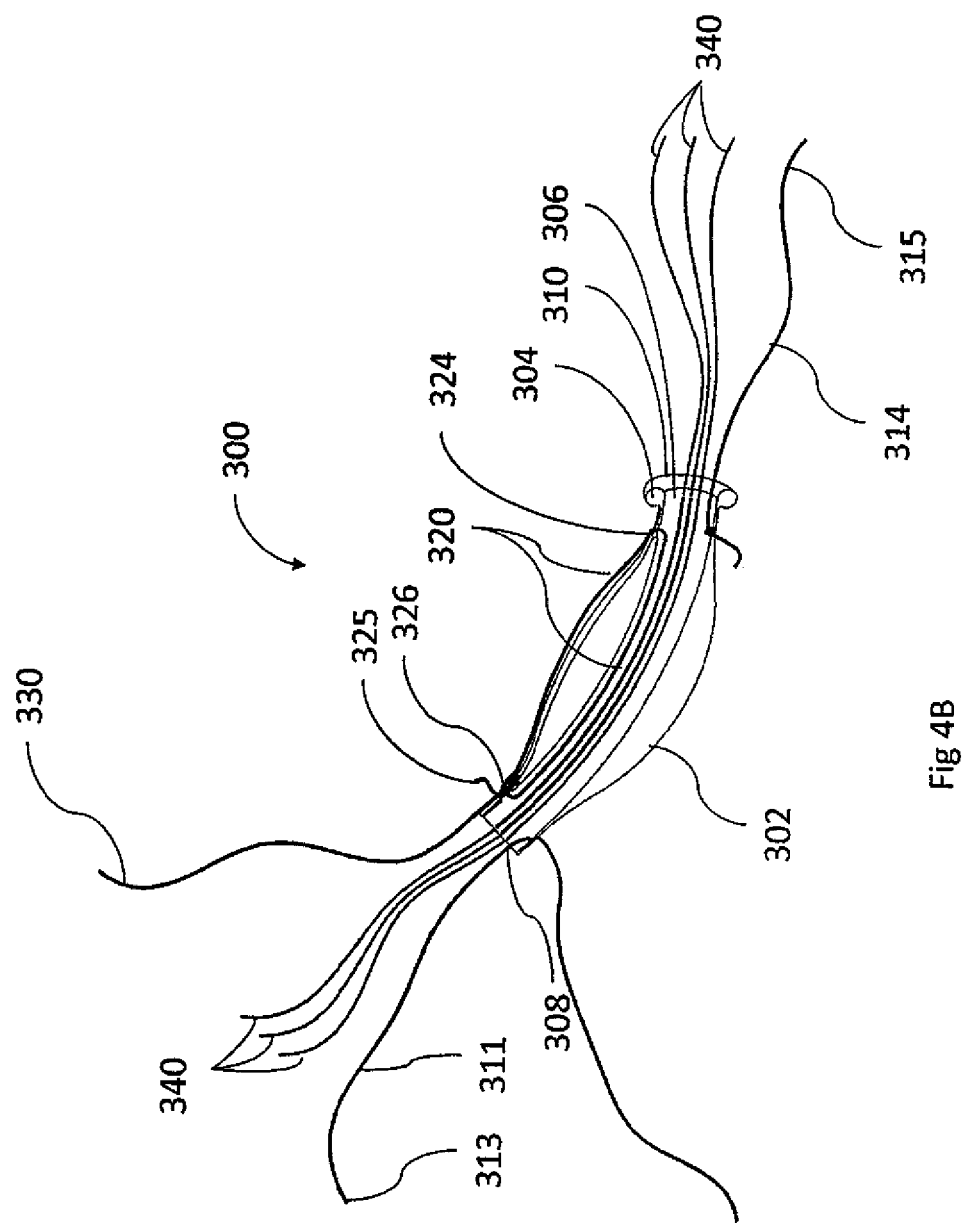

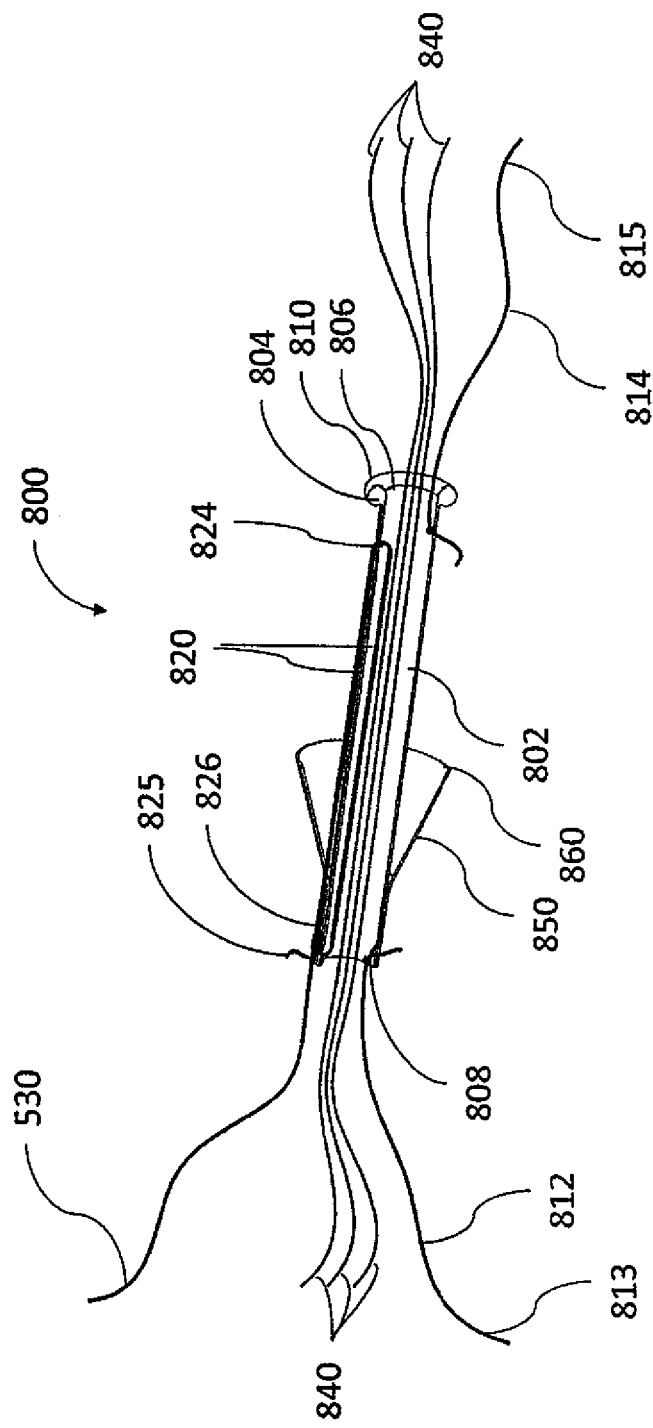

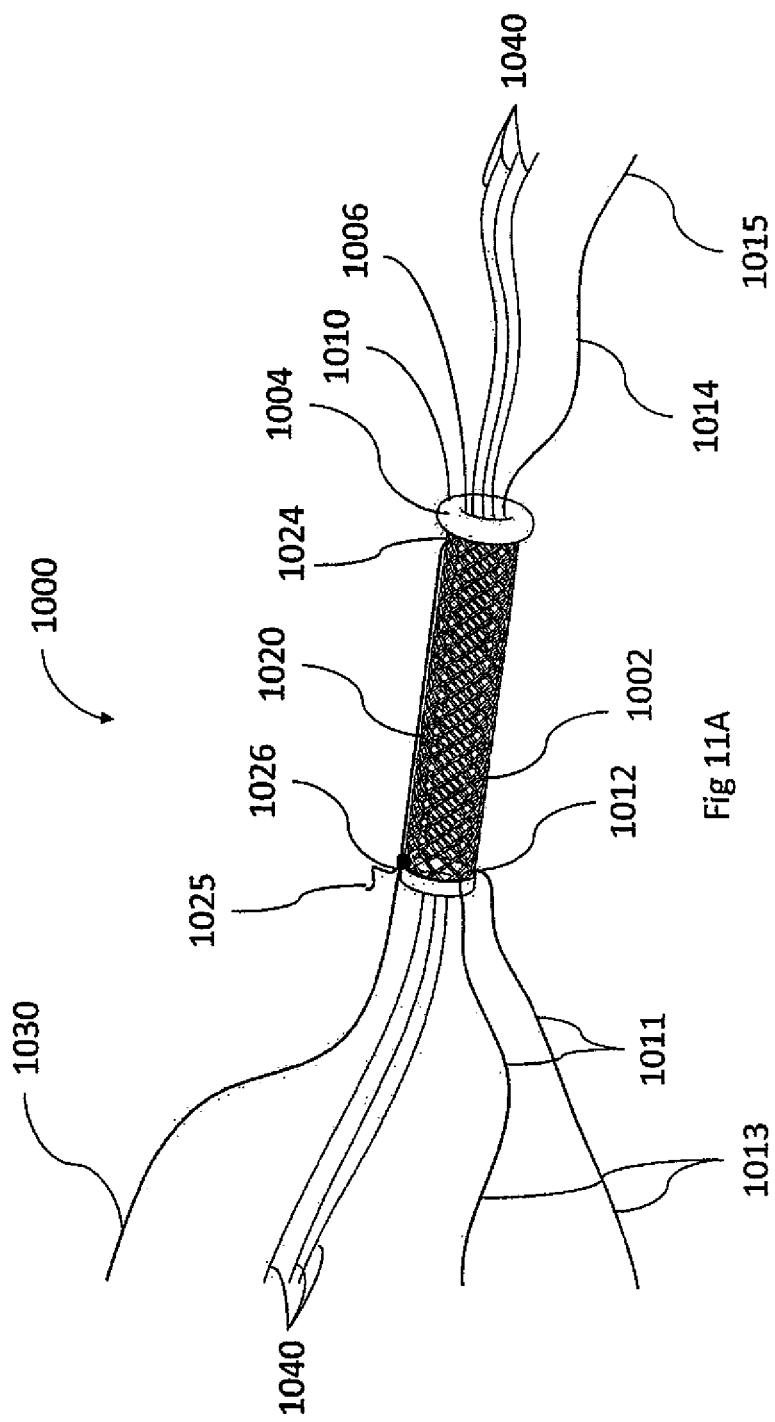

PADDED TRANSOSSEOUS SUTURE

REFERENCE TO RELATED APPLICATIONS

Reference is made to U.S. Provisional Patent Application Ser. No. 62/047,674 filed Sep. 9, 2014 and entitled "Padded Transosseous Suture", the disclosure of which is hereby incorporated by reference and priority of which is hereby claimed pursuant to 37 CFR 1.78(a) (4) and (5)(i).

FIELD OF THE INVENTION

The present invention relates to transosseous sutures and methods of use thereof.

BACKGROUND OF THE INVENTION

Various types of transosseous sutures are known in the art.

It is appreciated that the term "suture" as used throughout the description of the present invention refers to any suitable suture and also refers to a transfer wire or pull wire which is used to pull a suture through the bone. Typically, a transfer wire is used with the system and method of the present invention and is formed of Nitinol. Typically, a transfer wire used with the system and method of the present invention is folded over to form a loop at one end.

SUMMARY OF THE INVENTION

The present invention seeks to provide improved transosseous sutures.

There is thus provided in accordance with a preferred embodiment of the present invention a bone suture assembly including a flexible generally cylindrical sleeve, a plurality of lengths of suture extending through the generally cylindrical sleeve, and at least one sleeve securing thread associated with the generally cylindrical sleeve.

Preferably, the generally cylindrical sleeve is deformable. Additionally, the bone suture assembly includes at least one thread associated with the deformable cylindrical sleeve for selectively deforming the generally cylindrical sleeve. Additionally, the at least one thread for selective deforming includes a thread which is looped through apertures at opposite ends of the generally cylindrical sleeve and when pulled, draws the opposite ends towards each other, thereby deforming the generally cylindrical sleeve.

Preferably, the generally cylindrical sleeve is bendable but not deformable. Additionally or alternatively, the generally cylindrical sleeve is formed at one end thereof with a flange. Alternatively or additionally, the at least one sleeve securing thread includes at least one thread attached to the generally cylindrical sleeve at an end thereof. Additionally or alternatively, the at least one sleeve securing thread includes at least one thread looped through an aperture formed in the generally cylindrical sleeve at an end thereof. Also additionally or alternatively, the at least one sleeve securing thread includes at least one thread stitched along the generally cylindrical sleeve and having free ends extending beyond ends of the generally cylindrical sleeve.

In accordance with a preferred embodiment of the present invention the bone suture assembly also includes a flexible second outer sleeve affixed to and at least partially enclosing the flexible generally cylindrical sleeve. Additionally the flexible second outer sleeve is not deformable and includes a cylindrical portion and a conical portion, the cylindrical portion having a diameter approximately matching that of the exterior of the generally cylindrical sleeve and the conical portion extending outwardly of the generally cylindrical sleeve. Alternatively, the flexible second outer sleeve is generally cylindrical, is generally shorter than the generally cylindrical flexible sleeve and is deformable.

In accordance with a preferred embodiment the flexible generally cylindrical sleeve is a generally cylindrical braided sleeve. Additionally, the generally cylindrical sleeve may be pre-stressed to cause a torus shaped portion to be formed adjacent one end of the generally cylindrical braided sleeve and the pre-stressed generally cylindrical braided sleeve is stretchable to a generally cylindrical shape.

There is also provided in accordance with another preferred embodiment of the present invention a bone suture retaining method including engaging a suture with a bone engaging sleeve, inserting the suture and the bone engaging sleeve engaged thereby into a transosseous tunnel formed into a bone by pulling the bone engaging sleeve into the transosseous tunnel and retaining the suture and the bone engaging sleeve in the transosseous tunnel by virtue of the bone engaging sleeve being unable to fit through an aperture in the bone.

Preferably, the aperture in the bone is formed in bone cortex. Alternatively, the aperture in the bone is formed in bone medulla.

Preferably, the pulling is effected by pulling a flexible elongate element attached to the sleeve. Additionally or alternatively, the method includes deforming the bone engaging sleeve within the transosseous tunnel by pulling an elongated element attached to the bone engaging sleeve and thereby further engaging the bone engaging sleeve in the transosseous tunnel.

In accordance with a preferred embodiment of the present invention the bone suture retaining method includes deforming the bone engaging sleeve together with a flexible and deformable outer sleeve affixed thereto. Alternatively, the method includes expanding a flexible non-deformable conical outer sleeve affixed to the bone engaging sleeve following entry of the bone engaging sleeve into the transosseous tunnel.

In accordance with a preferred embodiment of the present invention the bone engaging sleeve is braided and the method includes pre-stressing the bone engaging sleeve to form a torus shaped portion adjacent one end thereof, stretching the bone engaging sleeve prior to the inserting and subsequent to the inserting and releasing the bone engaging sleeve thereby allowing re-expansion of the torus shaped portion.

There is thus further provided in accordance with another preferred embodiment of the present invention a suture including a threadable padding and at least one suture engaged with an outside surface of the padding, the padding having a shape to enable the suture to be threadable through an interior of the padding.

There is yet further provided in accordance with yet another preferred embodiment of the present invention, a suture including a threadable padding, a threader passed through the padding, the threader having a loop thereon at one end of the threader and a threader passed through the padding, the threader having a loop thereon at one end of the threader and at least one suture to be engaged through an outside surface of the padding and to be threaded through the loop, the padding having a shape to enable the loop to be threaded therethrough.

BRIEF DESCRIPTION OF THE DRAWINGS

The present invention will be understood and appreciated more fully from the following detailed description, taken in conjunction with the drawings in which:

FIGS. 4A & 4B are simplified respective pictorial and sectional illustrations of the transosseous suture assembly of FIGS. 3A & 3B in a second operative orientation;

FIGS. 8A & 8B are simplified respective pictorial and sectional illustrations of a transosseous suture assembly constructed and operative in accordance with a further preferred embodiment of the present invention in a first operative orientation;

FIGS. 11A & 11B are simplified respective pictorial and sectional illustrations of the transosseous suture assembly of FIGS. 10A & 10B in a second operative orientation;

Figure 1A:
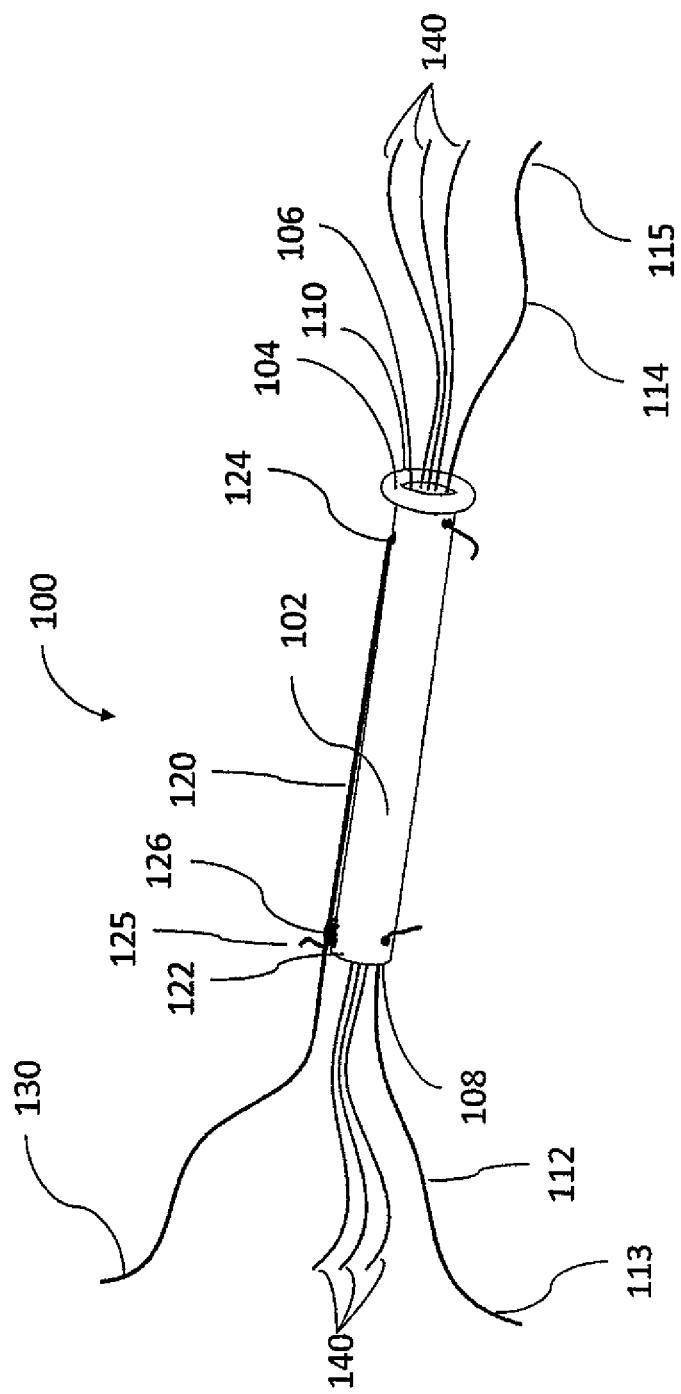
FIGS. 1A & 1B are simplified respective pictorial and sectional illustrations of a transosseous suture assembly constructed and operative in accordance with a preferred embodiment of the present invention in a first operative orientation.

It will be appreciated that for simplicity and clarity of illustration, segments shown in the figures have not necessarily been drawn to scale. For example, the dimensions of some of the segments may be exaggerated relative to other segments for clarity. Further, where considered appropriate, reference numerals may be repeated among the various figures to indicate corresponding or analogous segments.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Figure 1B:
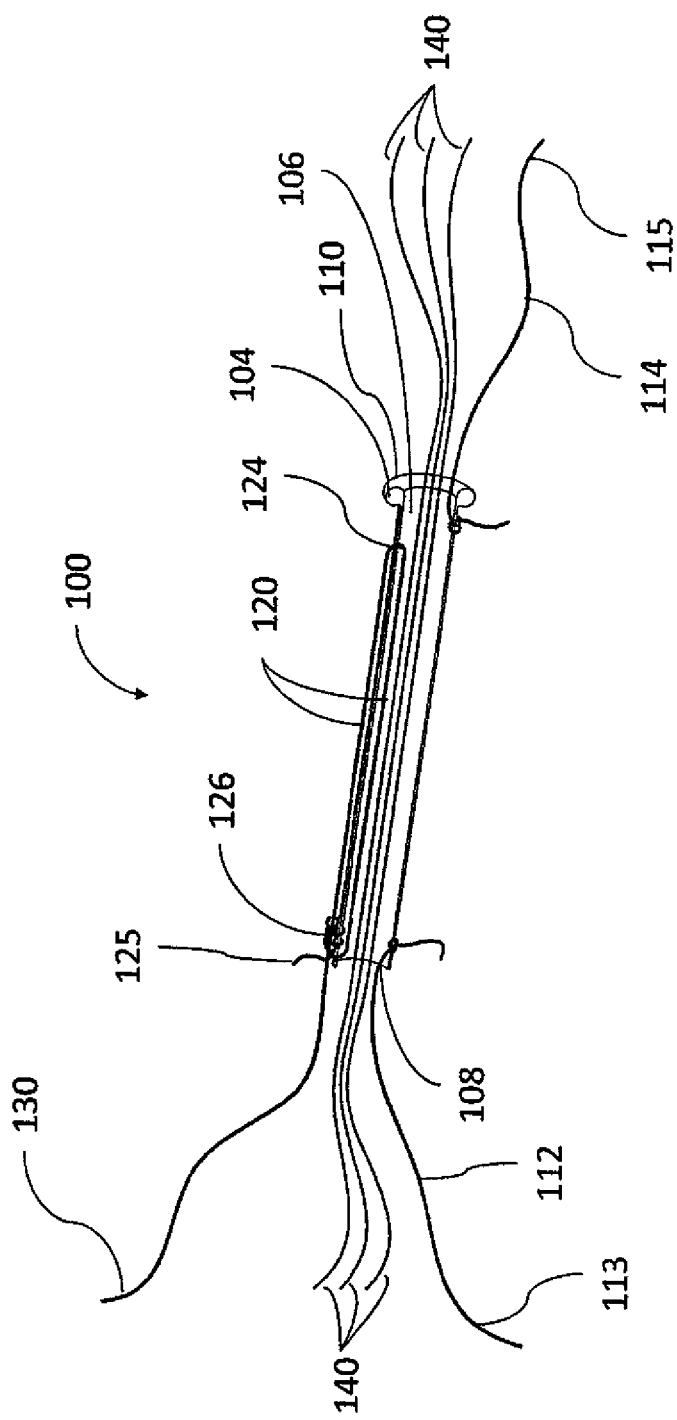

Reference is now made to FIGS. 1A & 1B, which are simplified respective pictorial and sectional illustrations of a transosseous suture assembly constructed and operative in accordance with a preferred embodiment of the present invention in a first operative orientation. As seen in FIGS. 1A & 1B, the transosseous suture assembly preferably includes a flexible and deformable sleeve 100, preferably formed of a polyester mesh such as polyester peek or nylon, or nitinol or cotton. Flexible and deformable sleeve 100 includes a generally circularly cylindrical main portion 102 having a first outer diameter of, typically slightly less than 3.2 mm in the first operative orientation where sleeve 100 is in a relaxed, extended state, and an outwardly extending flange portion 104, having a second outer diameter greater than the first outer diameter of main portion 102. A bore 106 extends from a first end 108 of the flexible and deformable sleeve 100 to a second end 110 of the flexible and deformable sleeve 100 at flange portion 104.

A first flexible thread 112 is attached to flexible and deformable sleeve 100 adjacent first end 108 thereof and has a free end 113 extending beyond first end 108 and a second flexible thread 114 is attached to flexible and deformable sleeve 100 adjacent second end 110 thereof and has a free end 115 extending beyond second end 110. A sleeve shortening thread 120 is preferably threaded through an aperture 126 at one end 122 of the flexible and deformable sleeve 100 adjacent first end 108 thereof and extends along most of the length of the sleeve to and through an aperture 124 adjacent the second end 110 of the flexible and deformable sleeve 100 and is looped back and fastened to first end 125 of the sleeve shortening thread 120 near aperture 126 and has a free end 130 extending beyond end 108.

A plurality of lengths of suture, typically three in number, here collectively designated by reference numeral 140, extend through flexible and deformable sleeve 100 and beyond both ends 108 and 110 thereof.

Figure 2A:
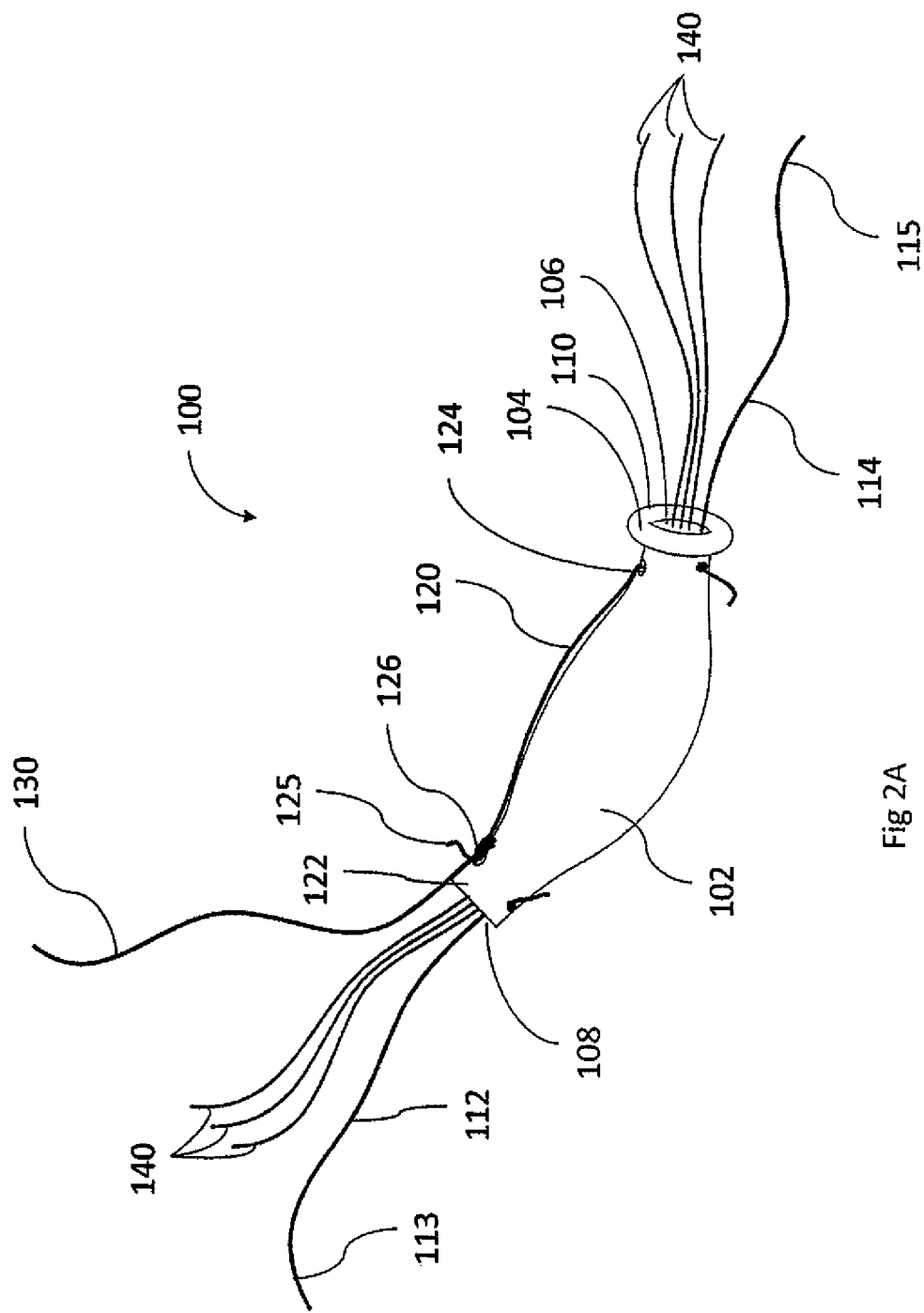
FIGS. 2A & 2B are simplified respective pictorial and sectional illustrations of the transosseous suture assembly of FIGS. 1A & 1B in a second operative orientation.
Figure 2B:
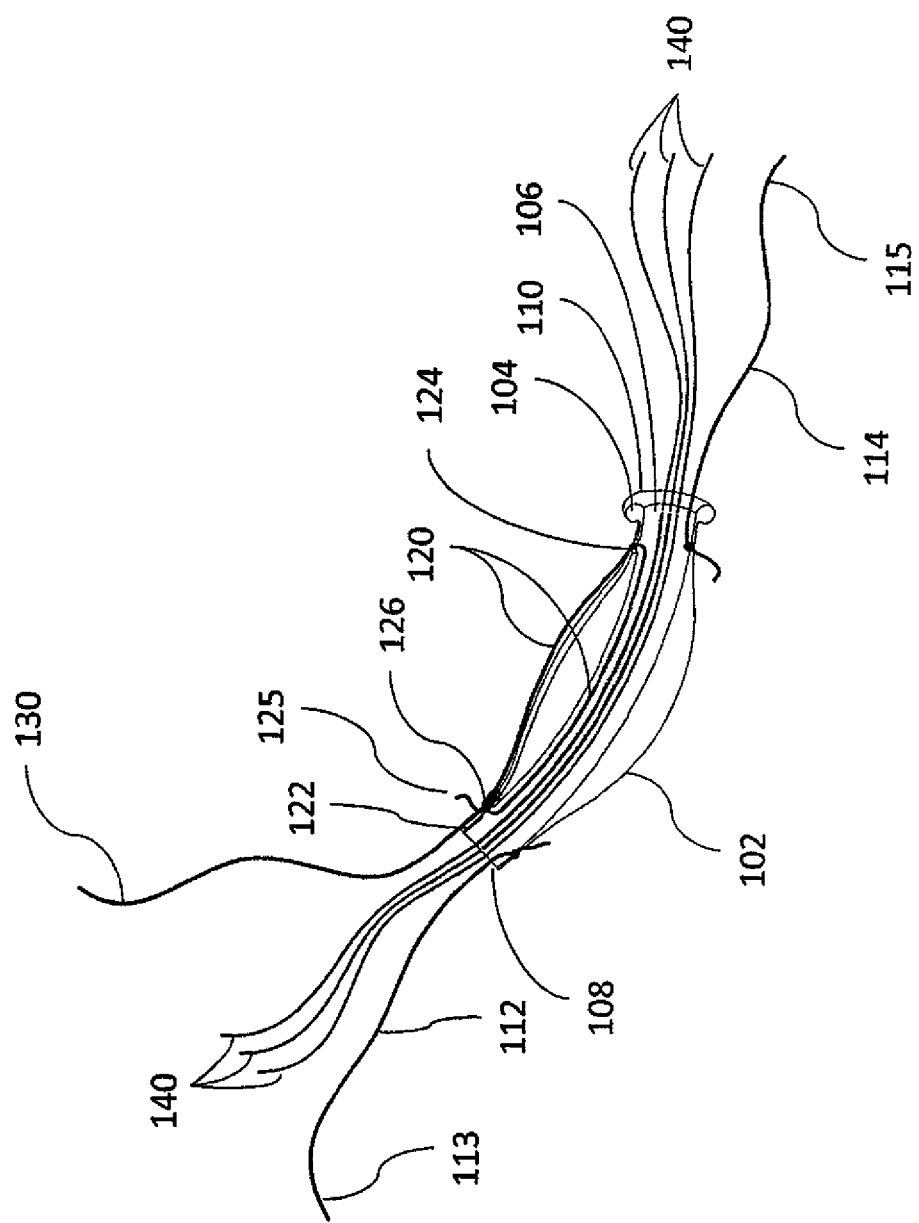

Reference is now made to FIGS. 2A & 2B, which are simplified respective pictorial and sectional illustrations of the transosseous suture assembly of FIGS. 1A & 1B in a second operative orientation, which results from pulling on the free end 130 of sleeve shortening thread 120 while holding flexible and deformable sleeve 100. As seen in FIGS. 2A and 2B and comparing them with FIGS. 1A & 1B, the overall length of the loop of sleeve shortening thread 120, which extends through apertures 124 and 126 is shortened, thus longitudinally shortening and deforming the flexible and deformable sleeve 100, typically as shown. This effectively widens the diameter of the flexible and deformable sleeve 100.

Figure 3A:
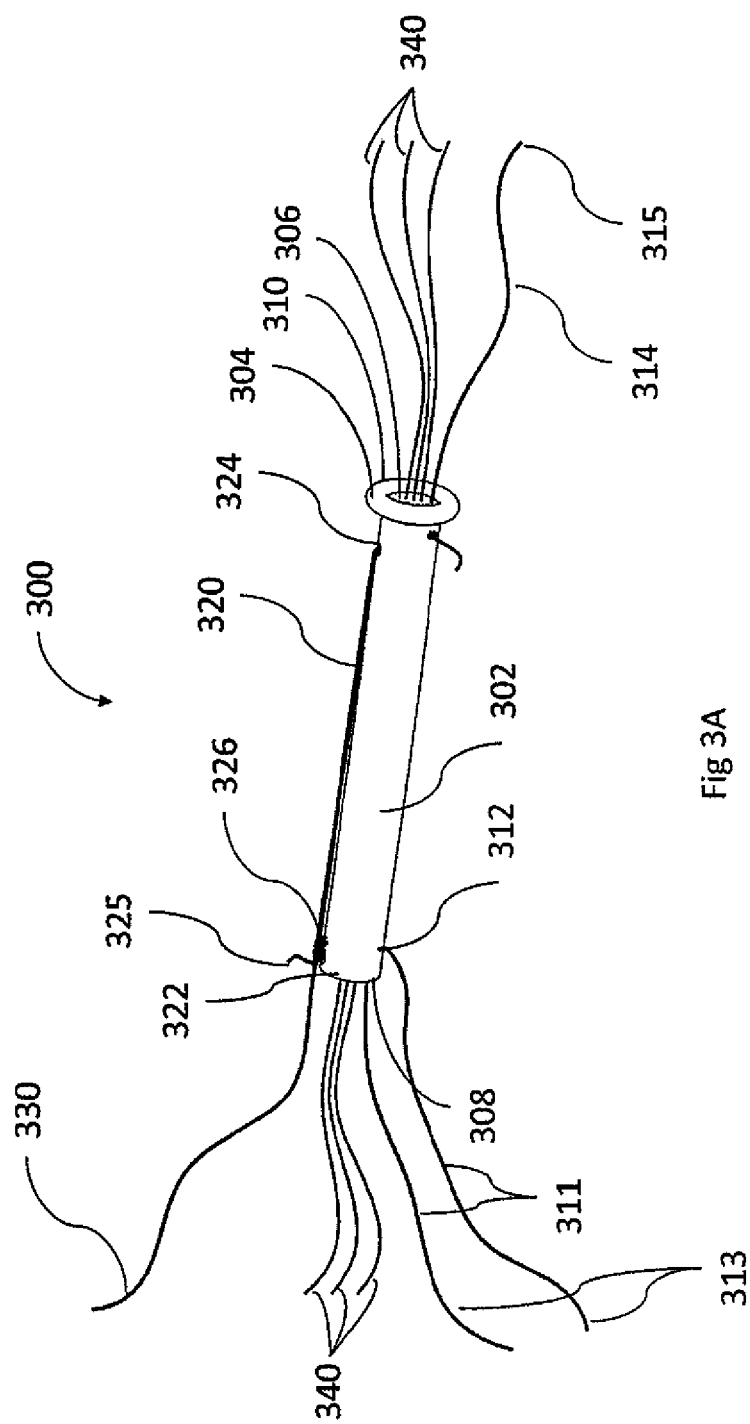
FIGS. 3A & 3B are simplified respective pictorial and sectional illustrations of a transosseous suture assembly constructed and operative in accordance with another preferred embodiment of the present invention in a first operative orientation.
Figure 3B:
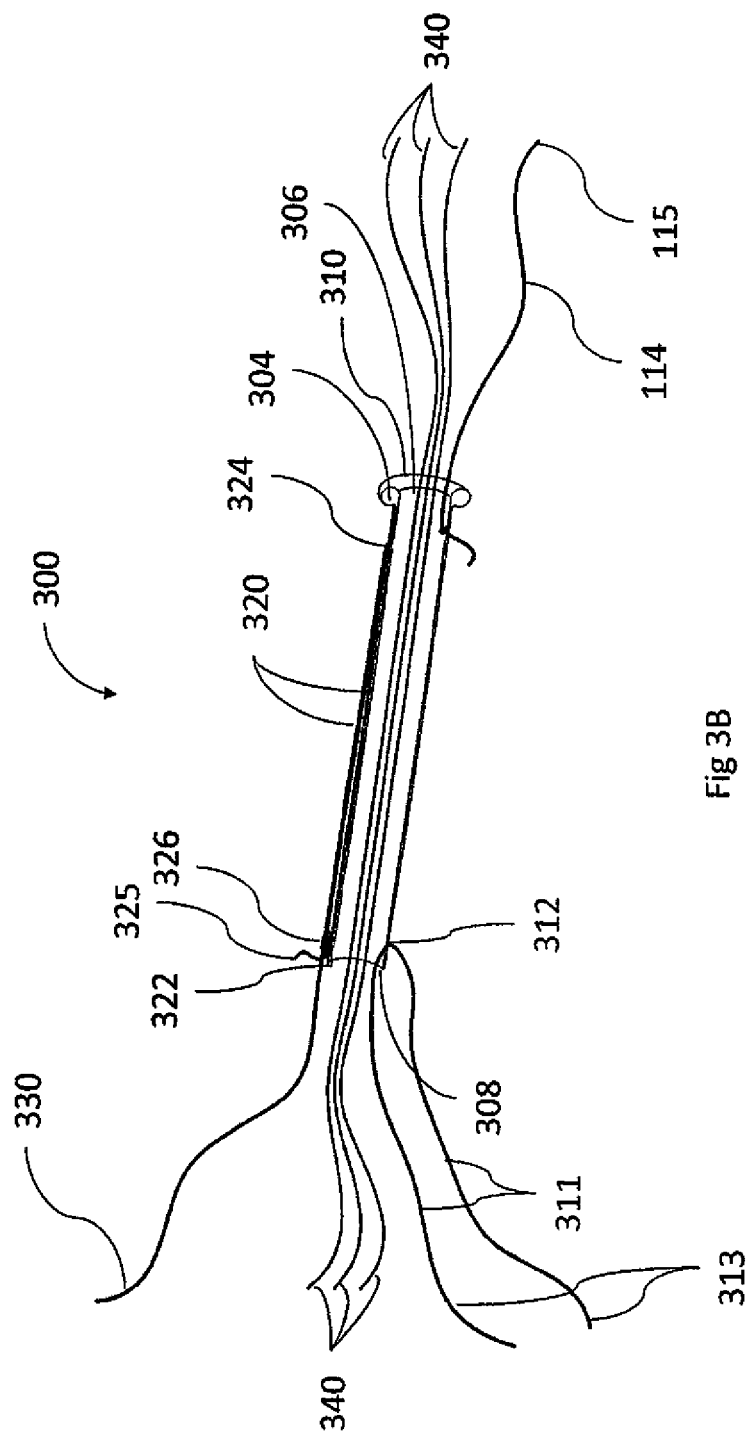

Reference is now made to FIGS. 3A & 3B, which are simplified respective pictorial and sectional illustrations of a transosseous suture assembly constructed and operative in accordance with another preferred embodiment of the present invention in a first operative orientation. As seen in FIGS. 3A & 3B, the transosseous suture assembly preferably includes a flexible and deformable sleeve 300, preferably formed of a polyester mesh such as polyester peek or nylon, or nitinol or cotton. Flexible and deformable sleeve 300 includes a generally circularly cylindrical main portion 302 having a first outer diameter of, typically slightly less than 3.2 mm in a relaxed, extended state, and an outwardly extending flange portion 304, having a second outer diameter greater than the first outer diameter of main portion 302. A bore 306 extends from a first end 308 of the flexible and deformable sleeve 300 to a second end 310 of the sleeve at flange portion 304.

A first flexible thread 311 is attached to flexible and deformable sleeve 300 by being looped through an aperture 312 formed therein adjacent first end 308 thereof and has two free ends 313 extending beyond first end 308 and a second flexible thread 314 is attached to flexible and deformable sleeve 300 adjacent second end 310 thereof and has a free end 315 extending beyond second end 310. A sleeve shortening thread 320 is preferably threaded through an aperture 326 at one end 322 of the flexible and deformable sleeve 300 adjacent first end 308 thereof and extends along most of the length of the sleeve to and through an aperture 324 adjacent the second end 310 of the flexible and deformable sleeve 300 and is looped back and fastened to first end 325 of the sleeve shortening thread 320 near aperture 326 and has a free end 330 extending beyond end 308.

A plurality of lengths of suture, typically three in number, here collectively designated by reference numeral 340, extend through flexible and deformable sleeve 300 and beyond both ends 308 and 310 thereof.

Figure 4A:
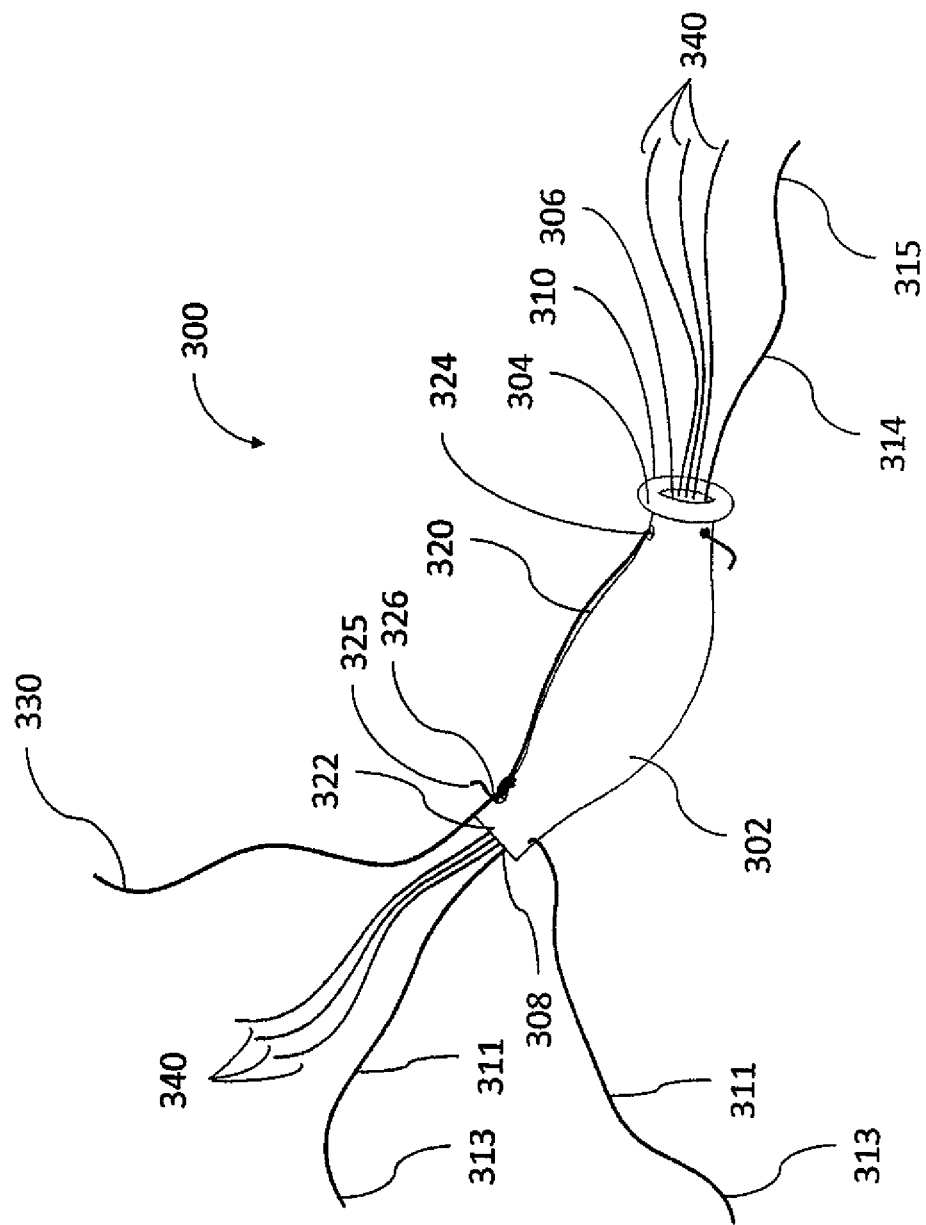

Reference is now made to FIGS. 4A & 4B, which are simplified respective pictorial and sectional illustrations of the transosseous suture assembly of FIGS. 3A & 3B in a second operative orientation, which results from pulling on the free end 330 of sleeve shortening thread 320 while holding flexible and deformable sleeve 300. As seen in FIGS. 4A and 4B and comparing them with FIGS. 3A & 3B, the overall length of the loop of sleeve shortening thread 320, which extends through apertures 324 and 326 is shortened, thus longitudinally shortening and deforming the flexible and deformable sleeve 300, typically as shown. This effectively widens the flexible and deformable sleeve 300 and increases the diameter thereof to a second outer diameter greater than the first outer diameter of the first operative orientation shown in FIGS. 3A & 3B.

Figure 5A:
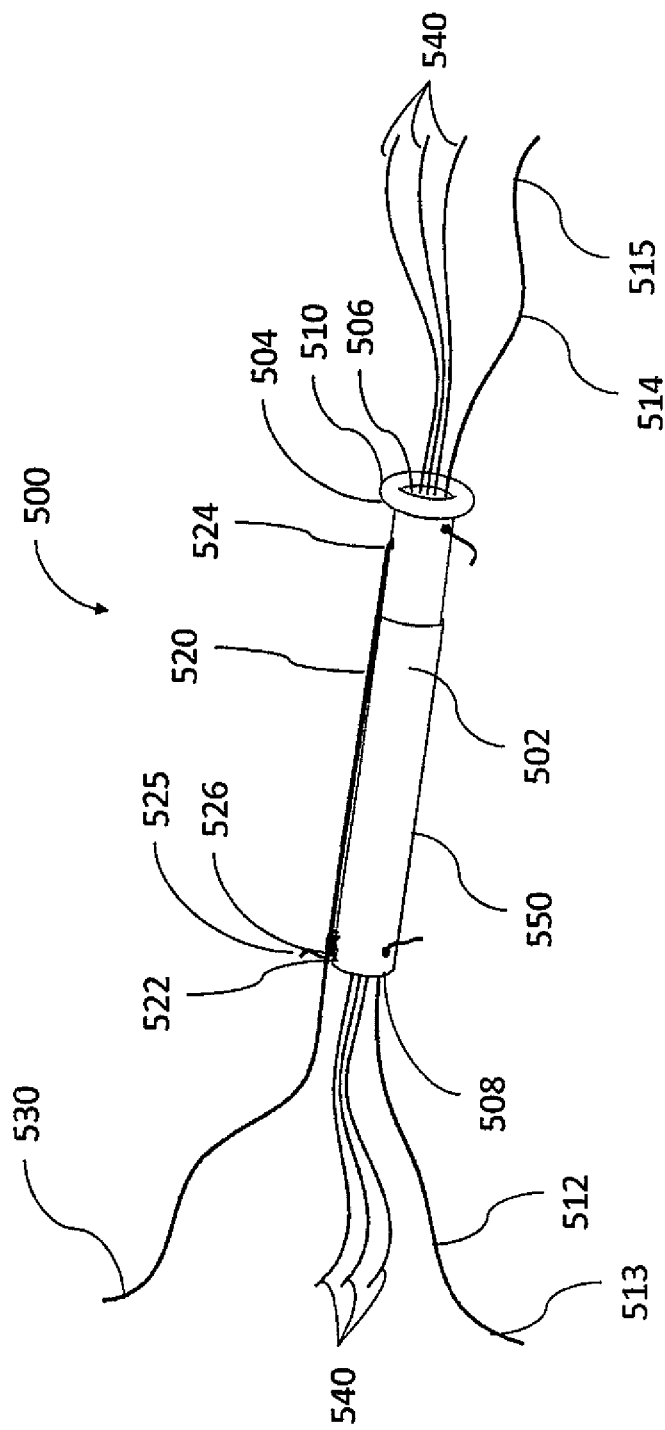
FIGS. 5A & 5B are simplified respective pictorial and sectional illustrations of a transosseous suture assembly constructed and operative in accordance with yet another preferred embodiment of the present invention in a first operative orientation.
Figure 5B:
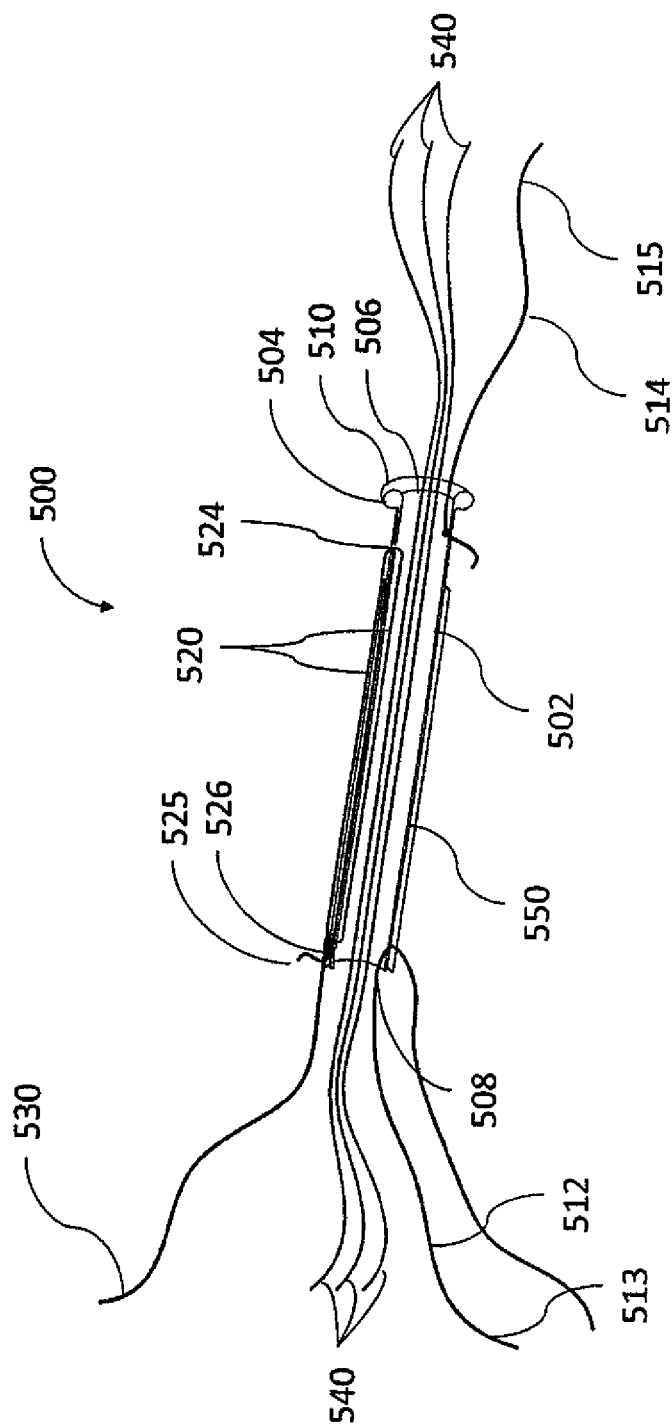

Reference is now made to FIGS. 5A & 5B, which are simplified respective pictorial and sectional illustrations of a transosseous suture assembly constructed and operative in accordance with yet another preferred embodiment of the present invention in a first operative orientation. As seen in FIGS. 5A & 5B, the transosseous suture assembly preferably includes a flexible and deformable sleeve 500, preferably formed of a polyester mesh such as polyester peek or nylon, or nitinol or cotton. Flexible and deformable sleeve 500 includes a generally circularly cylindrical main portion 502 having a first outer diameter of, typically slightly less than 3.2 mm in a relaxed, extended state, and an outwardly extending flange portion 504, having a second outer diameter greater than the first outer diameter of main portion 502. A bore 506 extends from a first end 508 of the flexible and deformable sleeve 500 to a second end 510 of the sleeve at flange portion 504.

A first flexible thread 512 is attached to flexible and deformable sleeve 500 adjacent first end 508 thereof and has a free end 513 extending beyond first end 508 and a second flexible thread 514 is attached to flexible and deformable sleeve 500 adjacent second end 510 thereof and has a free end 515 extending beyond second end 510. A sleeve shortening thread 520 is preferably threaded through an aperture 526 at one end 522 of the flexible and deformable sleeve 500 adjacent first end 508 thereof and extends along most of the length of the sleeve to and through an aperture 524 adjacent the second end 510 of the flexible and deformable sleeve 500 and is looped back and fastened to first end 525 of the sleeve shortening thread 520 near aperture 526 and has a free end 530 extending beyond end 508.

A plurality of lengths of suture, typically three in number, here collectively designated by reference numeral 540, extend through flexible and deformable sleeve 500 and beyond both ends 508 and 510 thereof. Attached near first end 508 of flexible and deformable sleeve 500 is an outer second sleeve 550 whose diameter is approximately equal to that of the exterior of the generally circularly cylindrical main portion 502 so that flexible and deformable sleeve 500 may be inserted into outer second sleeve 550 and become engaged within. Outer second sleeve 550 extends typically two-thirds to three-quarters the length of flexible and deformable sleeve 500 to end 560, is preferably formed of a polyester mesh such as polyester peek or nylon, or nitinol or cotton and is flexible and deformable. First flexible thread 512, in addition to being attached to flexible and deformable sleeve 500, is also attached to outer second sleeve 550 adjacent first end 508 of flexible and deformable sleeve 500.

Figure 6A:
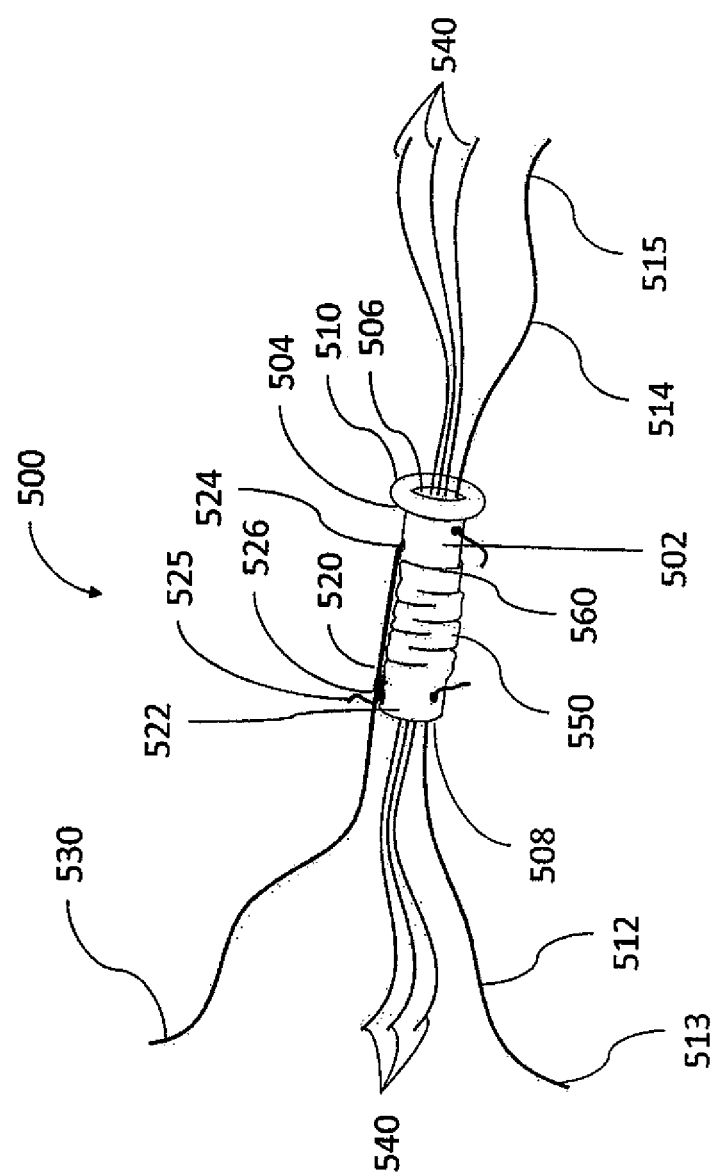
FIGS. 6A & 6B are simplified respective pictorial and sectional illustrations of the transosseous suture assembly of FIGS. 5A & 5B in a second operative orientation.
Figure 6B:
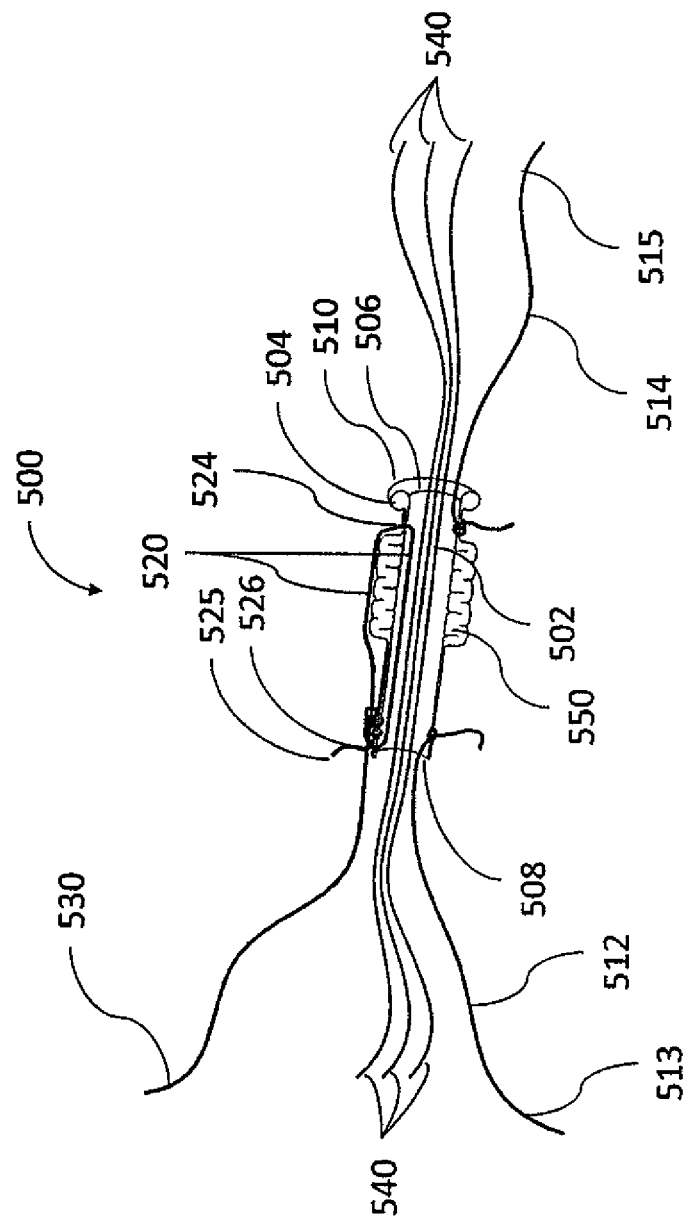

Reference is now made to FIGS. 6A & 6B, which are simplified respective pictorial and sectional illustrations of the transosseous suture assembly of FIGS. 5A & 5B in a second operative orientation, which results from pulling on the free end 530 of sleeve shortening thread 520 while holding flexible and deformable sleeve 500. As seen in FIGS. 6A and 6B and comparing them with FIGS. 5A & 5B, the overall length of the loop of sleeve shortening thread 520, which extends through apertures 524 and 526 is shortened, thus longitudinally shortening and deforming the flexible and deformable sleeve 500, typically as shown, with both the flexible and deformable sleeve 500 and the outer second sleeve 550 contracting between the end 560 of the outer second sleeve 550 and the first end 508 of the flexible and deformable sleeve. This effectively increases the diameter of the combined flexible and deformable sleeve 500 and the outer second sleeve 550 between the end 560 of the outer second sleeve 550 and the first end 508 of the flexible and deformable sleeve 500. Inclusion of the outer second sleeve 550 significantly increases the total amount of material in the contracted region between the end 560 of the outer second sleeve 550 and the first end 508 of the flexible and deformable sleeve, as compared to only the flexible and deformable sleeve 500, and thus results in the dual sleeve having a greater total diameter.

Figure 7A:
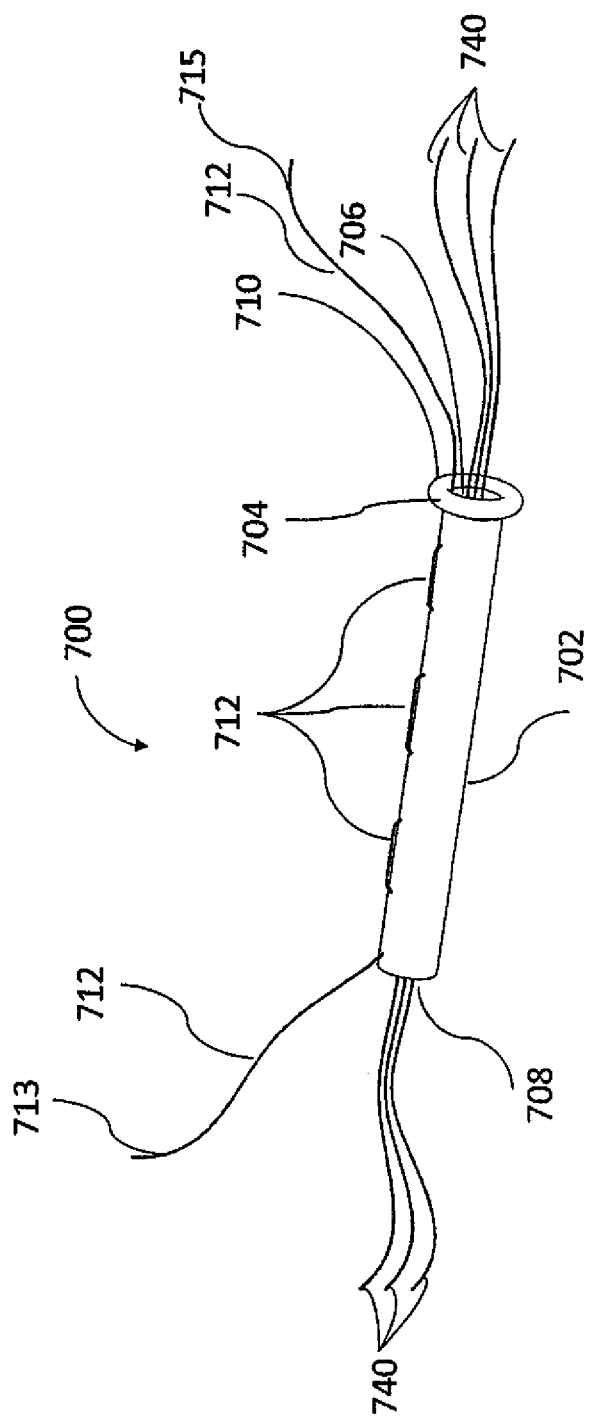
FIGS. 7A & 7B are simplified respective pictorial and sectional illustrations of a transosseous suture assembly constructed and operative in accordance with still another preferred embodiment of the present invention in a first operative orientation.
Figure 7B:
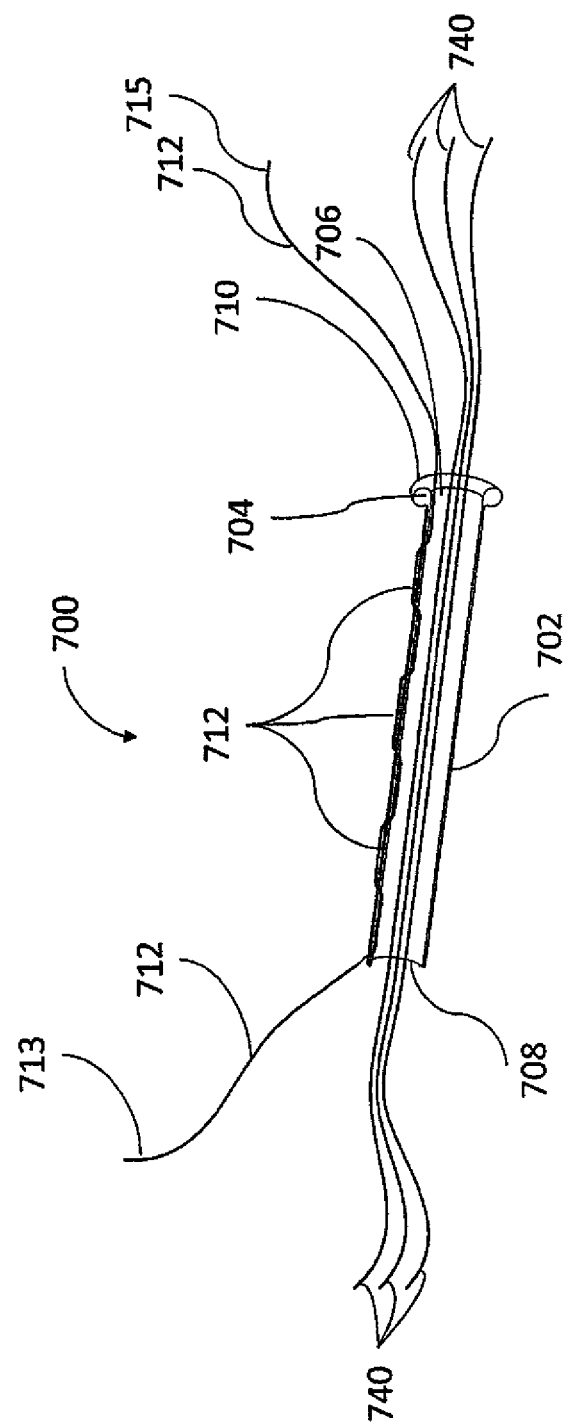

Reference is now made to FIGS. 7A & 7B, which are simplified respective pictorial and sectional illustrations of a transosseous suture assembly constructed and operative in accordance with still another preferred embodiment of the present. As seen in FIGS. 7A & 7B, the transosseous suture assembly preferably includes a flexible sleeve 700, preferably formed of a polyester mesh such as polyester peek or nylon, or nitinol or cotton. Flexible sleeve 700 including a generally circularly cylindrical main portion 702 having a first outer diameter of, typically slightly less than 3.2 mm, and an outwardly extending flange portion 704, having a second outer diameter greater than the first outer diameter of main portion 702. A bore 706 extends from a first end 708 of the flexible sleeve 700 to a second end 710 of the sleeve.

A flexible thread 712 is loosely stitched along the length of flexible sleeve 700 from a location adjacent first end 708 thereof and has a free end 713 extending beyond first end 708 to a location adjacent second end 710 thereof and has a free end 715 extending beyond second end 710. Flexible thread 712, in this embodiment, is an alternative to having first and second threads attached to flexible sleeve 700 (see FIG. 13D below); flexible sleeve 700 may be manufactured with flexible thread 712 imbedded, thus obviating the need for manual affixing or looping of threads into flexible sleeve 700. A plurality of lengths of suture, typically three in number, here collectively designated by reference numeral 740, extend through flexible sleeve 700 and beyond both ends 708 and 710 thereof.

Figure 8A:
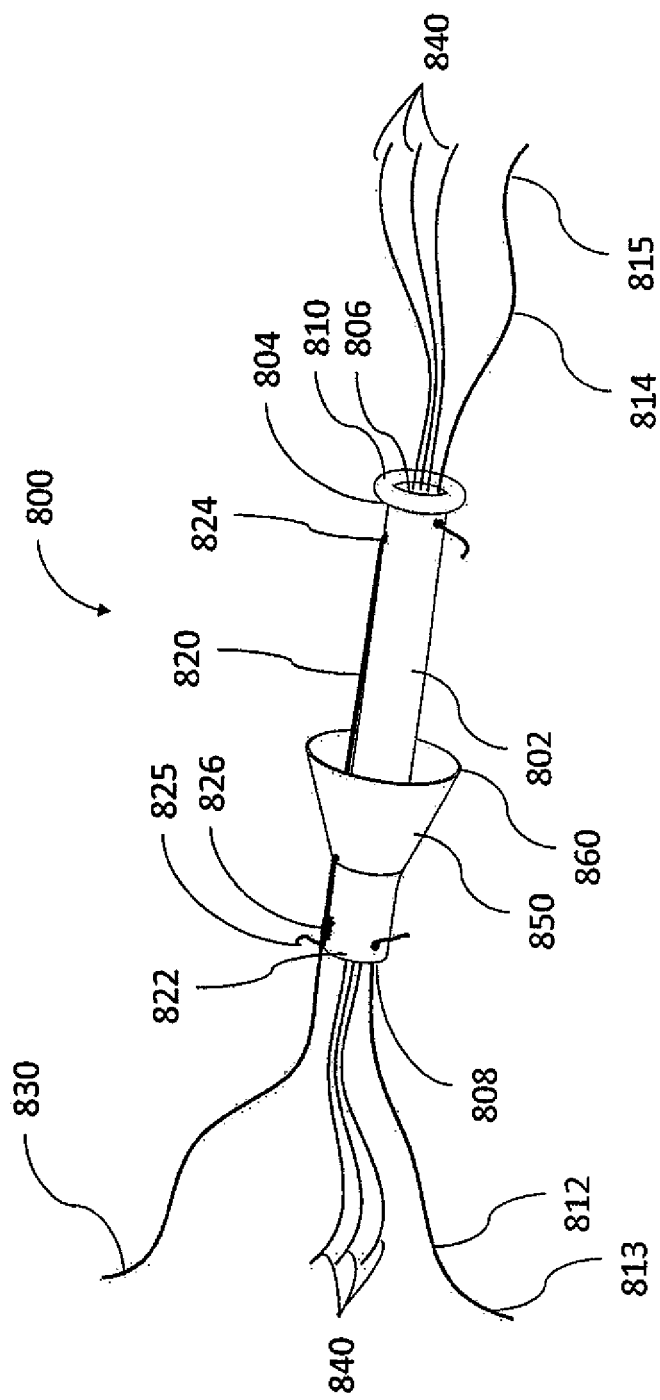

Reference is now made to FIGS. 8A & 8B, which are simplified respective pictorial and sectional illustrations of a transosseous suture assembly constructed and operative in accordance with a further preferred embodiment of the present. As seen in FIGS. 8A & 8B, the transosseous suture assembly preferably includes a flexible sleeve 800, preferably formed of a polyester mesh such as polyester peek or nylon, or nitinol or cotton. Flexible sleeve 800 including a generally circularly cylindrical main portion 802 having a first outer diameter of, typically slightly less than 3.2 mm, and an outwardly extending flange portion 804, having a second outer diameter greater than the first outer diameter of main portion 802. A bore 806 extends from a first end 808 of the flexible sleeve 800 to a second end 810 of the sleeve at flange portion 804.

A first flexible thread 812 is attached to flexible sleeve 800 adjacent first end 808 thereof and has a free end 813 extending beyond first end 808 and a second flexible thread 814 is attached to flexible sleeve 800 adjacent second end 810 thereof and has a free end 815 extending beyond second end 810. Optionally as shown, a tightening thread 820 is threaded through an aperture 826 at one end 822 of the flexible sleeve 800 adjacent first end 808 thereof and extends along most of the length of the sleeve to and through an aperture 824 adjacent the second end 810 of the flexible sleeve 800 and is looped back and fastened to first end 825 of the tightening thread 820 near aperture 826 and has a free end 830 extending beyond end 808.

A plurality of lengths of suture, typically three in number, here collectively designated by reference numeral 840, extend through flexible sleeve 800 and beyond both ends 808 and 810 thereof. Attached near first end 808 of flexible sleeve 800 is a flared outer second sleeve 850, having a cylindrical portion and a conical portion whose cylindrical portion has a diameter approximately matching that of the exterior of the generally circularly cylindrical main portion 802 near the first end 808 and whose diameter increases toward the second end 810 of the flexible sleeve 800. Flared outer second sleeve 850 has a horn-like shape, open at end 860, and is flexible.

Figure 9A:
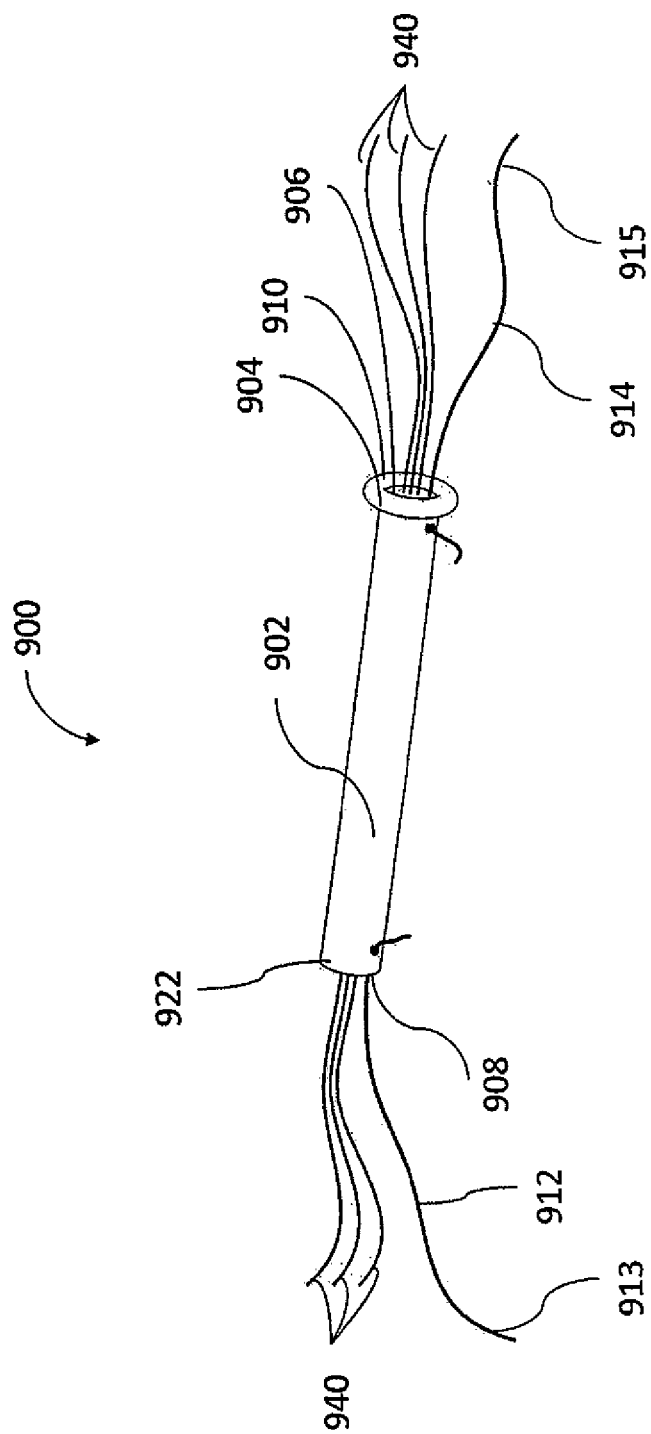
FIGS. 9A & 9B are simplified respective pictorial and sectional illustrations of a transosseous suture assembly constructed and operative in accordance with a yet further preferred embodiment of the present invention in a first operative orientation.
Figure 9B:
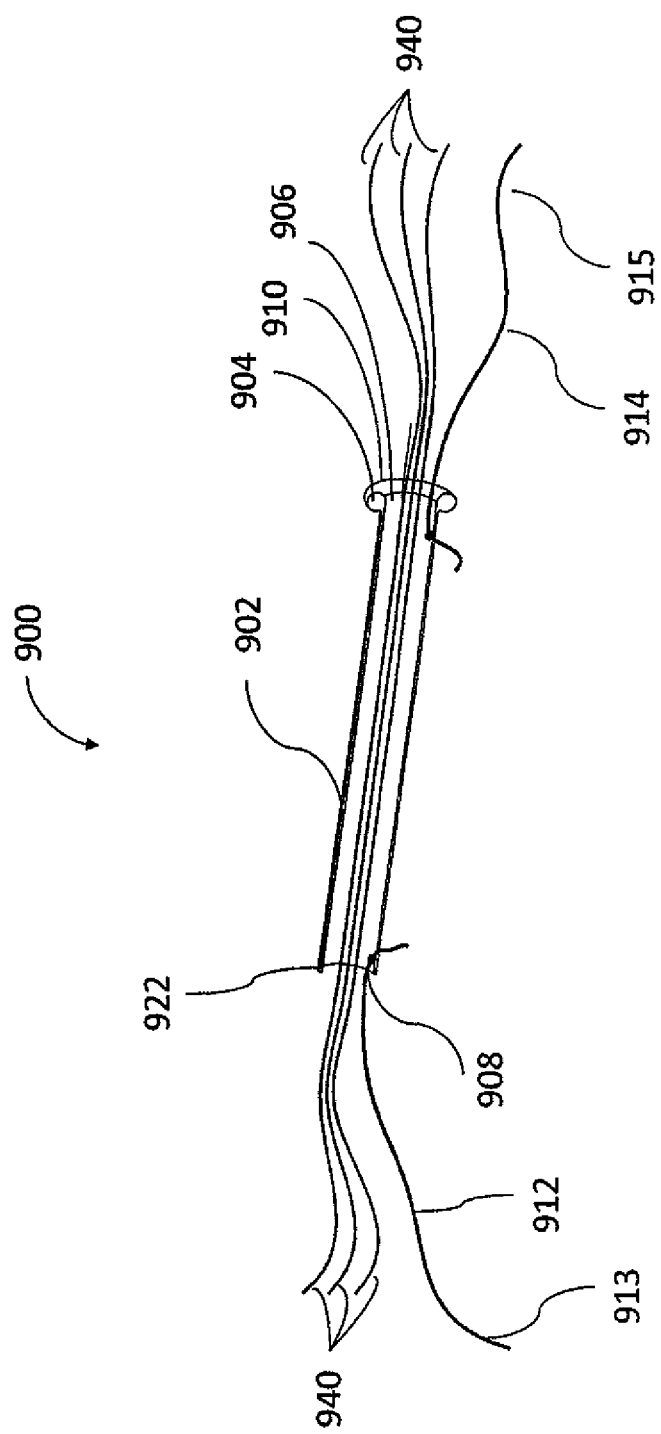

Reference is now made to FIGS. 9A & 9B, which are simplified respective pictorial and sectional illustrations of a transosseous suture assembly constructed and operative in accordance with a yet further preferred embodiment of the present. As seen in FIGS. 9A & 9B, the transosseous suture assembly preferably includes a flexible sleeve 900, preferably formed of a polyester mesh such as polyester peek or nylon, or nitinol or cotton. Flexible and deformable sleeve 900 includes a generally circularly cylindrical main portion 902 having a first outer diameter of, typically slightly less than 3.2 mm, and an outwardly extending flange portion 904, having a second outer diameter greater than the first outer diameter of main portion 902. A bore 906 extends from a first end 908 of the flexible sleeve 900 to a second end 910 of the sleeve.

A first flexible thread 912 is attached to flexible sleeve 900 adjacent first end 908 thereof and has a free end 913 extending beyond first end 908 and a second flexible thread 914 is attached to flexible sleeve 900 adjacent second end 910 thereof and has a free end 915 extending beyond second end 910. A plurality of lengths of suture, typically three in number, here collectively designated by reference numeral 940, extend through flexible sleeve 900 and beyond both ends 908 and 910 thereof.

Figure 10A:
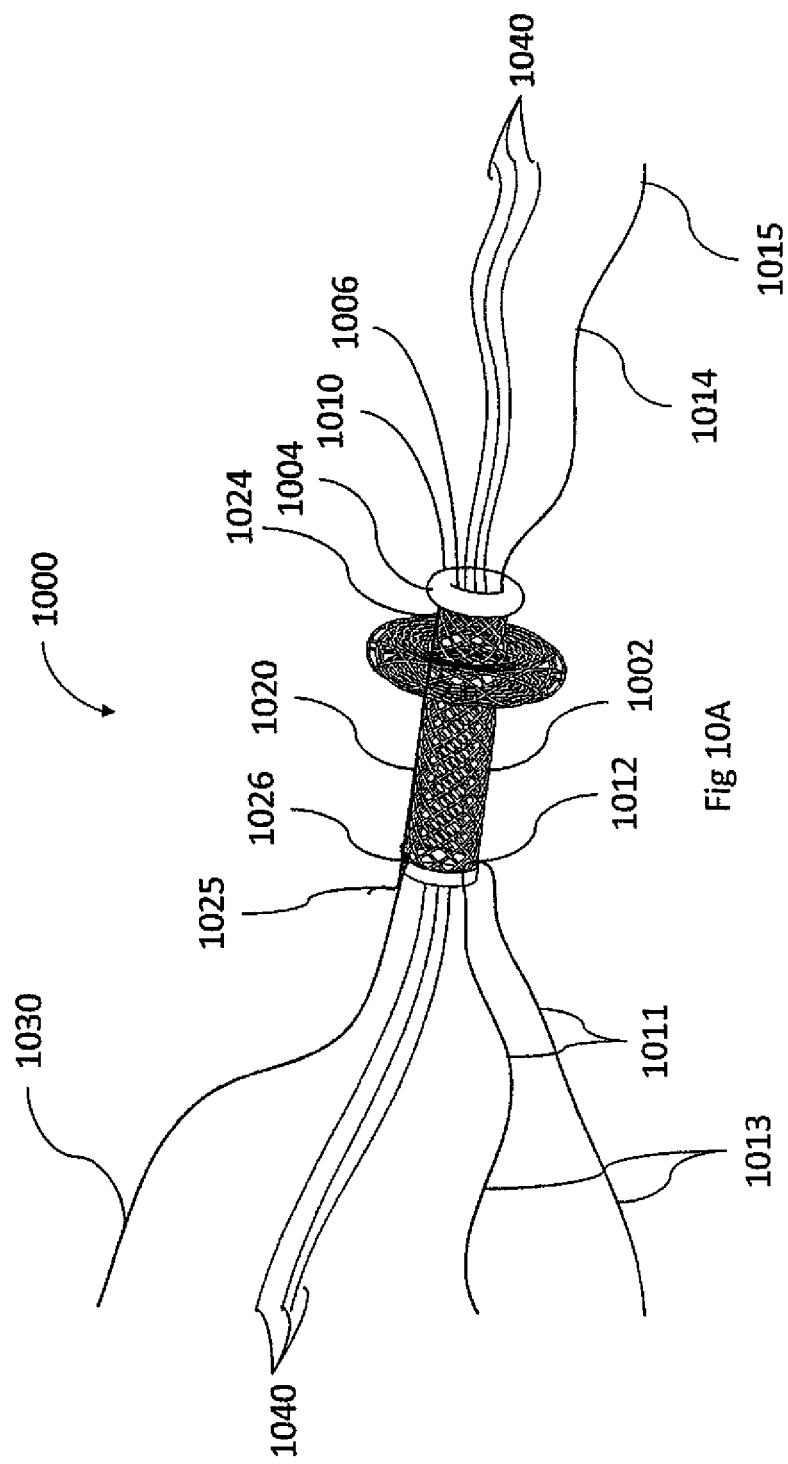
FIGS. 10A & 10B are simplified respective pictorial and sectional illustrations of a transosseous suture assembly constructed and operative in accordance with a still further preferred embodiment of the present invention in a first operative orientation.
Figure 10B:
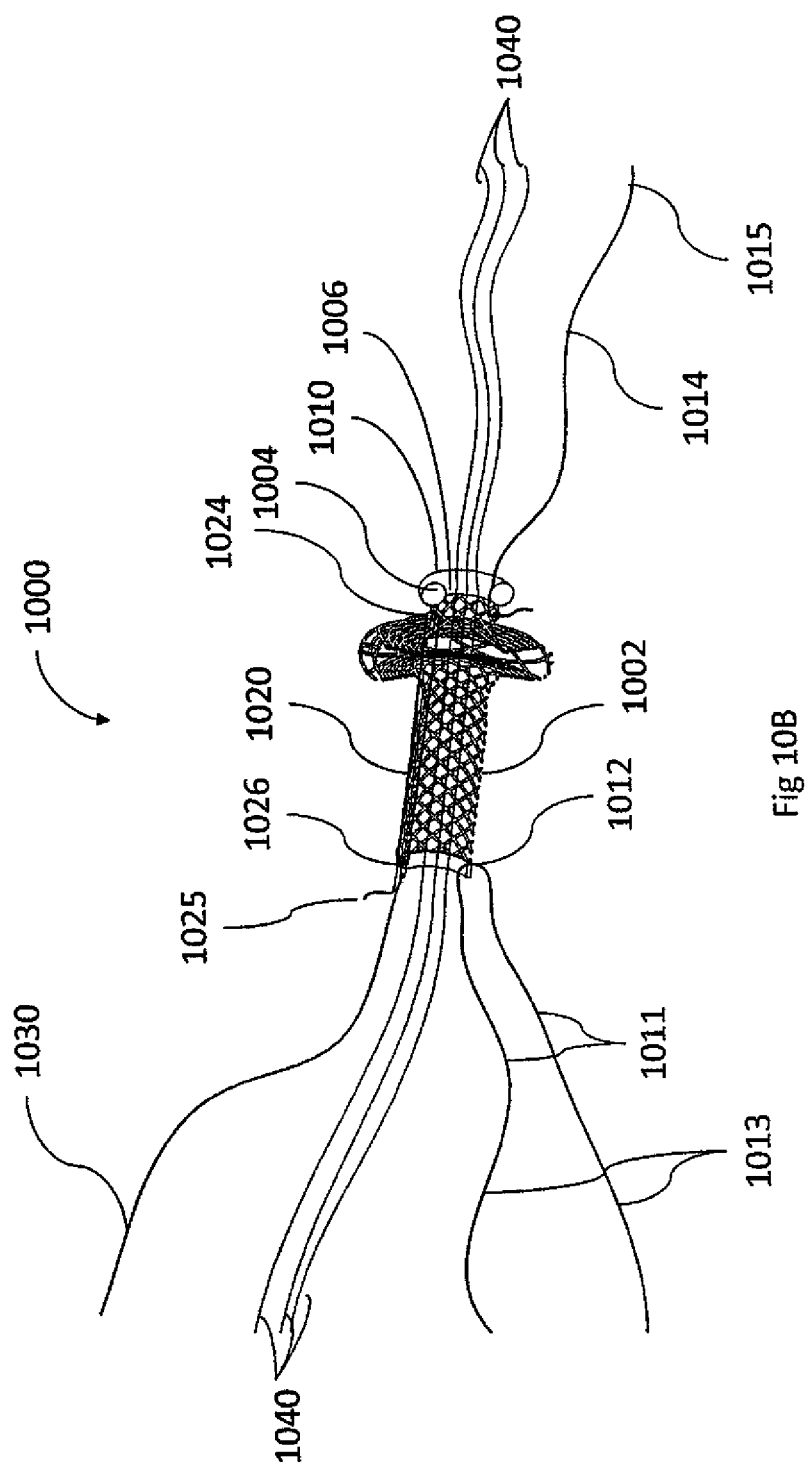

Reference is now made to FIGS. 10A & 10B, which are simplified respective pictorial and sectional illustrations of a transosseous suture assembly constructed and operative in accordance with a still further preferred embodiment of the present invention in a first operative orientation. As seen in FIGS. 10A & 10B, the transosseous suture assembly preferably includes a flexible and deformable braided sleeve 1000, preferably formed of a polyester mesh such as polyester peek or nylon, or nitinol or cotton. Flexible and deformable braided sleeve 1000 including a generally circularly cylindrical main portion 1002 having a first outer diameter of, typically slightly less than 3.2 mm in a relaxed, extended state, and an outwardly extending flange portion 1004, having a second outer diameter greater than the first outer diameter of main portion 1002. A bore 1006 extends from a first end 1008 of the flexible and deformable braided sleeve 1000 to a second end 1010 of the sleeve at flange portion 1004.

A first flexible thread 1011 is attached to flexible and deformable braided sleeve 1000 by being looped through an aperture 1012 formed therein adjacent first end 1008 thereof and has two free ends 1013 extending beyond first end 1008 and a second flexible thread 1014 is attached to flexible and deformable braided sleeve 1000 adjacent second end 1010 thereof and has a free end 1015 extending beyond second end 1010. In an alternative embodiment, first flexible thread 1011 is affixed to flexible and deformable braided sleeve 1000 at aperture 1012 adjacent first end 1008 and has a free end 1013 extending beyond first end 1008. A tightening thread 1020 is preferably threaded through an aperture 1026 at one end 1022 of the flexible and deformable braided sleeve 1000 adjacent first end 1008 thereof and extends along most of the length of the sleeve to and through an aperture 1024 adjacent the second end 1000 of the flexible and deformable braided sleeve 1000 and is looped back and fastened to first end 1025 of the tightening thread 1020 near aperture 1026 and has a free end 1030 extending beyond end 1008.

A plurality of lengths of suture, typically three in number, here collectively designated by reference numeral 1040, extend through flexible and deformable braided sleeve 1000 and beyond both ends 1008 and 1010 thereof. Adjacent flange 1004 at second end 1010 of the flexible and deformable braided sleeve 1000, the flexible and deformable braided sleeve 1000 has been pre-stressed or pre-formed and, as shown, a torus shaped portion 1050 is made in the flexible and deformable braided sleeve 1000 with an outer diameter typically about 6 mm. As shown in FIGS. 10A & 10B, the pre-stressed flexible and deformable braided sleeve 1000 is in a relaxed state. In an alternative embodiment, flexible and deformable braided sleeve 1000 is not pre-stressed and is thus generally circularly cylindrical with no torus shaped portion 1050 pre-formed.

Figure 11B:
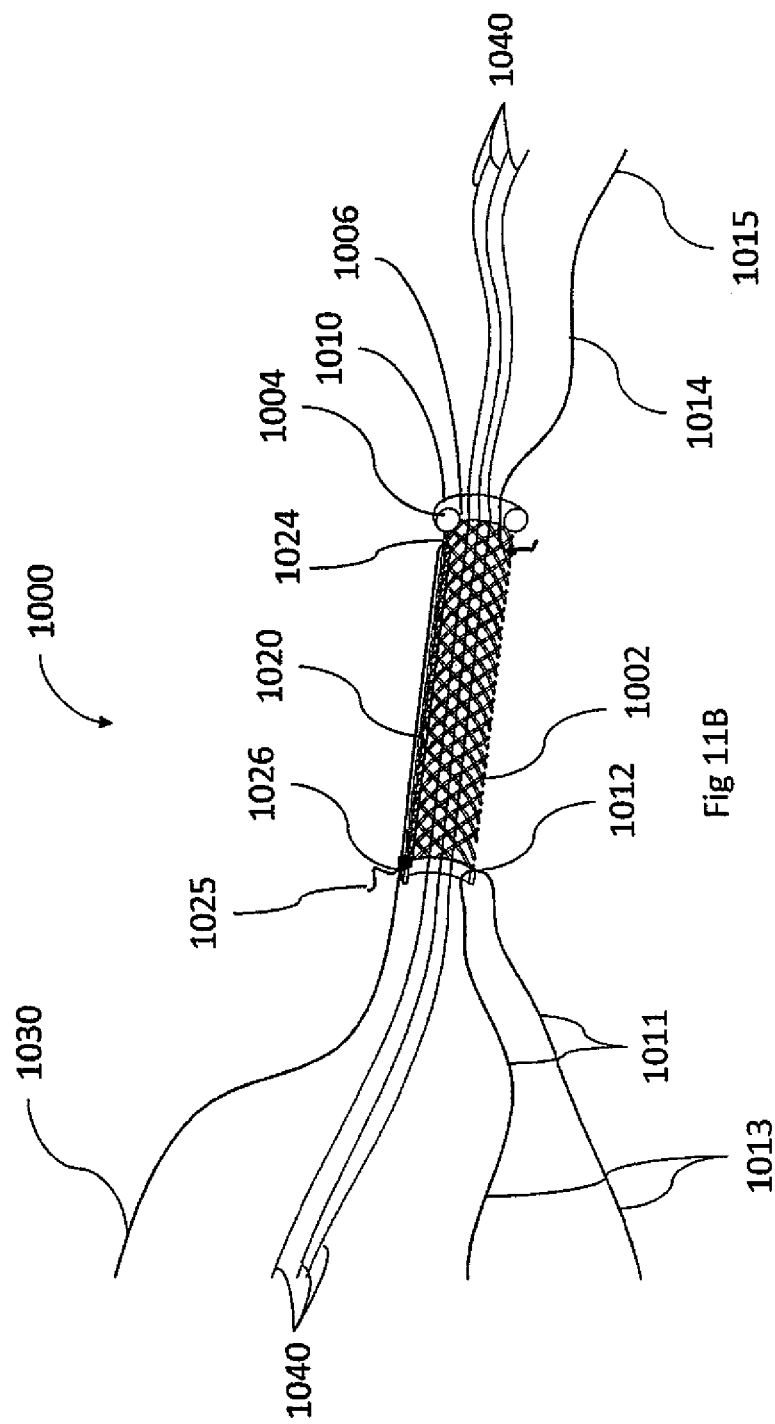

Reference is now made to FIGS. 11A & 11B, which are simplified respective pictorial and sectional illustrations of the transosseous suture assembly of FIGS. 10A & 10B in a second operative orientation, which results from pulling on the free ends 1013 of first flexible thread 1011 while holding second flexible thread 1014. As seen in FIGS. 11A and 11B and comparing them with FIGS. 10A & 10B, the overall length of the flexible and deformable braided sleeve 1000 is increased, thus longitudinally stretching the flexible and deformable braided sleeve 1000, specifically flattening the pre-formed torus shape 1050, typically as shown. This effectively narrows the diameter of the flexible and deformable braided sleeve 1000 to a near uniform diameter, typically slightly less than 3.2 mm.

It is understood that, in an alternative embodiment with a non pre-stressed flexible and deformable braided sleeve 1000, the flexible and deformable braided sleeve 1000 will appear as is shown in FIGS. 11A & 11B, when in a relaxed state.

Figure 12A:
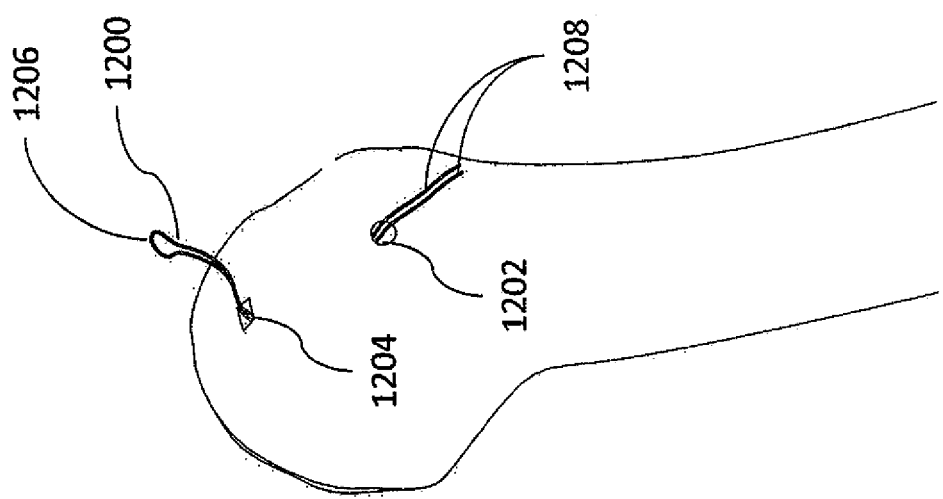
FIGS. 12A, 12B, 12C, 12D and 12E are together a simplified illustration of some preliminary stages of the insertion of a transosseous suture assembly of any of the embodiments illustrated in FIGS. 1A-11B.

Reference is now made to FIGS. 12A, 12B, 12C, 12D & 12E, which are together a simplified illustration of some preliminary stages of the insertion of a transosseous suture assembly of any of the embodiments illustrated in FIGS. 1A-11B;

Referring specifically to FIG. 12A, which is a simplified illustration of a first stage of the insertion of a transosseous suture assembly into a bone, it is seen that a first looped transfer wire 1200 has been inserted into a side bore 1202 made in a bone and has been pulled through the bone until it exits a top bore 1204 made in the bone. Loop 1206 of first looped transfer wire 1200 extends outside top bore 1204 and a pair of loose ends 1208 of first looped transfer wire 1200 extend outside side bore 1202. It is noted (shown below in FIGS. 13A-13G) that top bore 1204 is generally narrower than side bore 1202 and intersects side bore 1202 within the osseous portion of the bone at nearly a right angle.

Figure 12B:
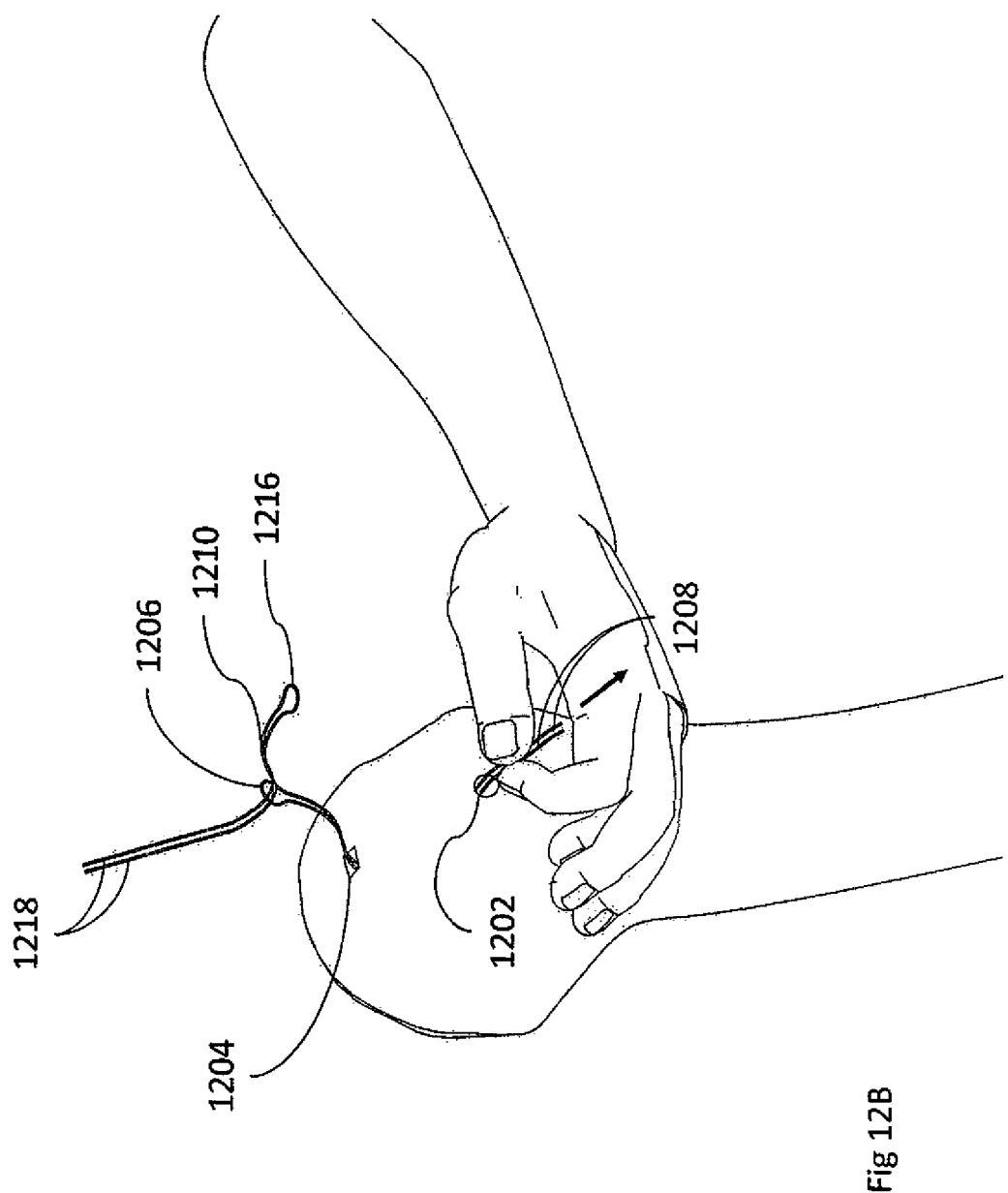

Referring now specifically to FIG. 12B, which is a simplified illustration of a second stage of the insertion of a transosseous suture assembly into a bone, it is seen that a second looped transfer wire 1210 has been inserted into loop 1206 of first looped transfer wire 1200 extending outside top bore 1204 in bone. Loop 1216 of second looped transfer wire 1210 extends through loop 1206 of first looped transfer wire 1200 while a pair of loose ends 1218 of second looped transfer wire 1210 extend outside other side of loop 1206 of first looped transfer wire 1200. Following this second stage of the insertion of a transosseous suture assembly into a bone, the first looped transfer wire 1200 is pulled through the bone from the top bore 1204 through the side bore 1202, pulling the second looped transfer wire 1210 through the bone with it.

Figure 12C:
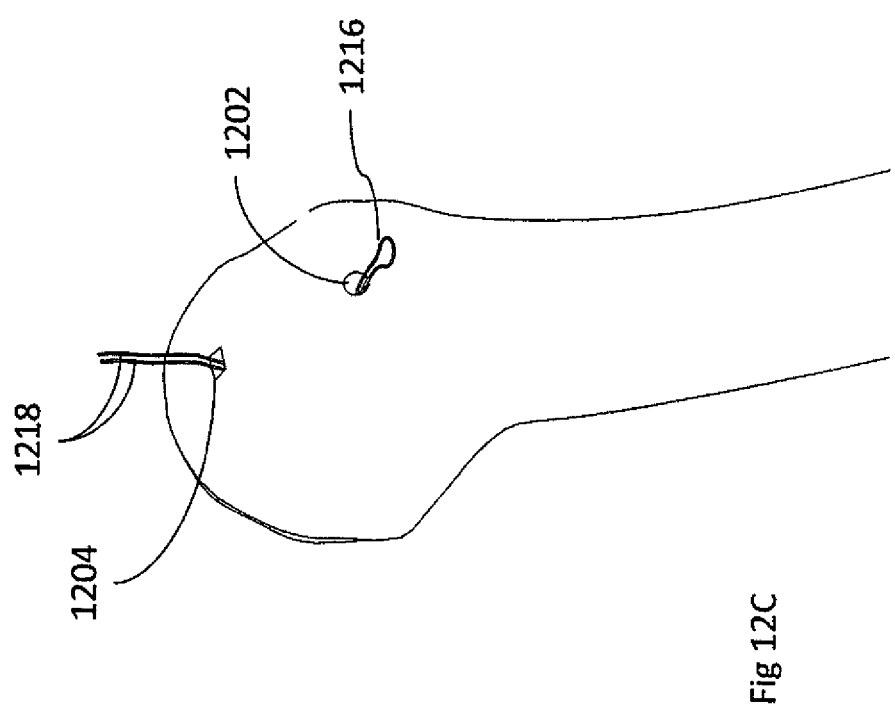

Reference is now made to FIG. 12C, which is a simplified illustration of a third stage of the insertion of a transosseous suture assembly into a bone. In this stage it is seen that the second looped transfer wire 1210 has been pulled through the top bore 1204 (as described above in reference to FIG. 12B) and out the side bore 1202; loop 1216 now extends outside side bore 1202 with the pair of loose ends 1218 extending out of top bore 1204 resulting in the second looped transfer wire 1210 being in the reverse position of the first looped transfer wire 1200, as seen in FIG. 12A.

Figure 12D:
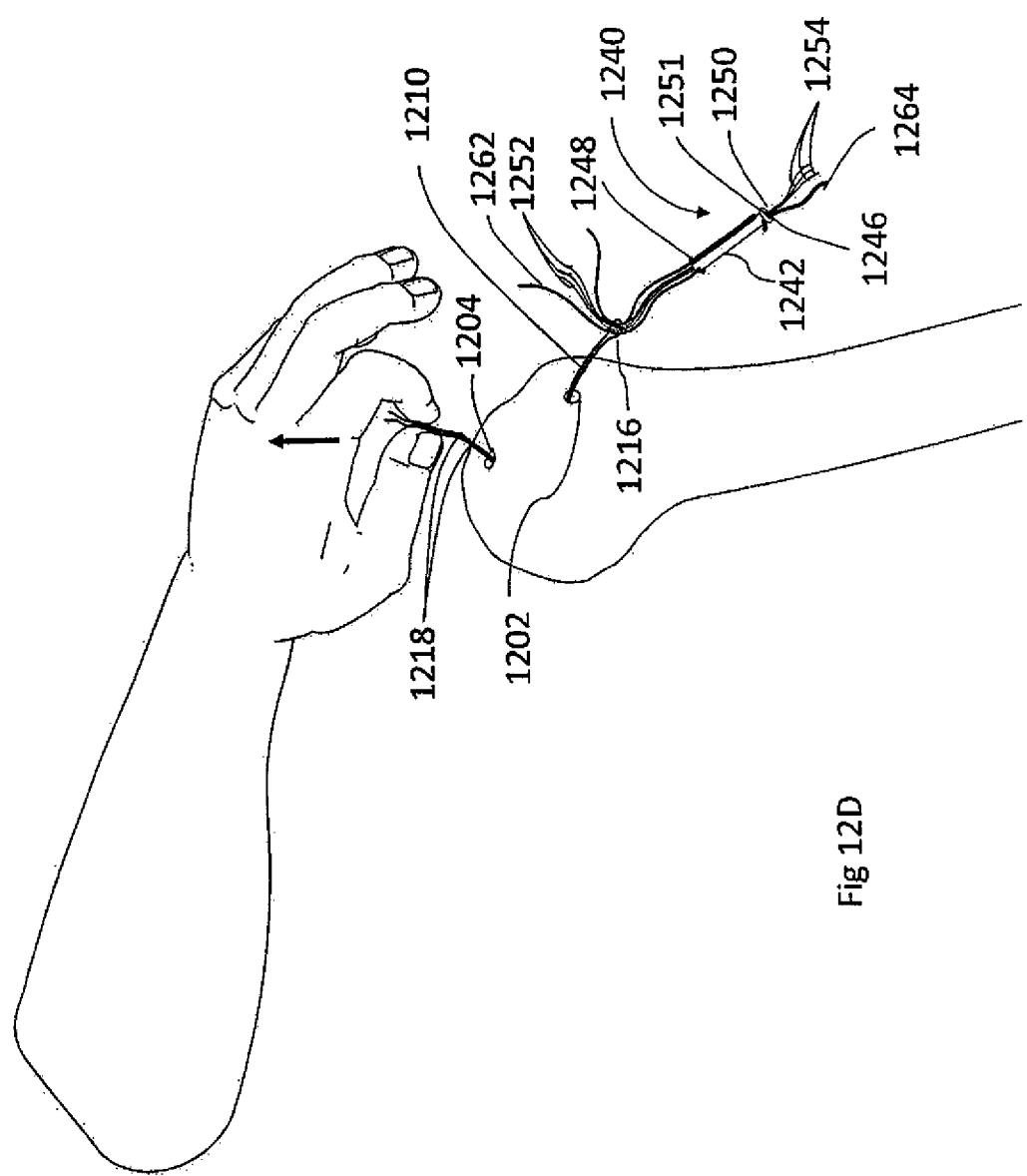

Referring now specifically to FIG. 12D, which is a simplified illustration of a fourth stage of the insertion of a transosseous suture assembly into a bone, it is seen that a transosseous suture 1240 has been inserted through the loop 1216 of the second looped transfer wire 1210, which extends outside side bore 1202 in bone. Transosseous suture 1240 comprises a generally cylindrical portion 1242 with a plurality of sutures 1244, typically three, threaded through a bore 1246 formed in generally cylindrical portion 1242 and extending from first end 1248 to second end 1250 of generally cylindrical portion 1242 of transosseous suture 1240, and an outwardly extending flange portion 1251. It is understood that, when referring here to the transosseous suture 1240, reference is being made to any one of the above defined flexible sleeve embodiments of the current invention. Sutures 1244 have free ends 1252 at first end 1248, shown extending through loop 1216 of the second looped transfer wire 1210, and free ends 1254 extending from second end 1250 of the generally cylindrical portion 1242 of the transosseous suture 1240. Following this fourth stage of the insertion of a transosseous suture assembly into a bone, the second looped transfer wire 1210 is pulled through the bone from the side bore 1202 through the top bore 1204, pulling the transosseous suture 1240 into the side bore 1202 in the bone. Sutures 1262 and 1264, now extending from top bore 1204 and side bore 1202, respectively, are affixed and/or looped through apertures in transosseous suture 1240.

Figure 12E:
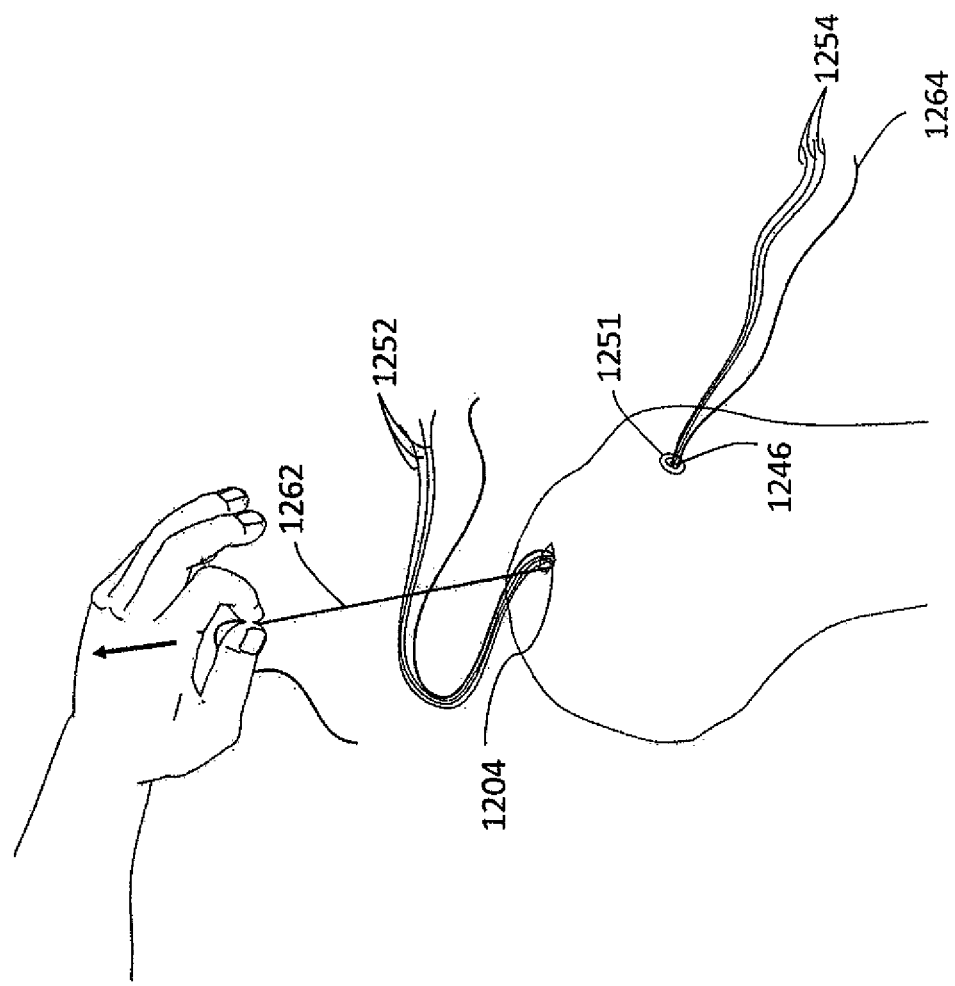

Reference is now made to FIG. 12E, which is a simplified pictorial illustration of a fifth stage in the insertion of a transosseous suture assembly into a bone. It is seen that transosseous suture 1240 has become engaged within side bore 1202 in the bone and sutures 1244 have been pulled through top bore 1204 in bone. In this stage, the free ends 1252 of the transosseous suture 1240 extend outside the top bore 1204, while the free ends 1254 at the opposite end of the transosseous suture 1240 extend outside the side bore 1202 in the bone. Transosseous suture 1240 has become engaged in side bore 1204 and cannot progress into top bore 1204 because top bore 1204 is narrow and because nearly right angle formed at intersection of top bore 1204 and side bore 1202 both inhibit passage, as described above in reference to FIG. 12A, and because of outwardly extending flange portion 1251 which inhibits complete passage of the transosseous suture 1240 into the side bore 1204, being generally wider than the diameter of the side bore 1204. It is understood and described below that, some embodiments may become more tightly engaged in bone by pulling on locking suture 1280, when locking suture 1280 is present.

Reference is now made to FIGS. 13A, 13B, 13C & 13D, 13E, 13F & 13G, which are simplified sectional illustrations of the penultimate stage of the insertion of the transosseous suture assembly, as described above in relation to FIG. 12E, of the various embodiments illustrated in FIGS. 1A-2B, FIGS. 3A-4B, FIGS. 5A-6B, FIGS. 7A & B, FIGS. 8A & B, FIGS. 9A & B and FIGS. 10A-11B, respectively. Each of FIGS. 13A, 13B, 13C, 13D, 13E. 13F & 13G demonstrate the effect on the sleeve of pulling a suture attached to the sleeve from the top bore, engaging the sleeve within the side bore of the bone. It is understood that each of FIGS. 13A-13G are respective sectional illustrations of FIG. 12E, one illustration per preferred embodiment of the present invention, as described and shown in connection with FIGS. 1A-11B Reference is now made to FIG. 13A, which is a simplified sectional illustration of the penultimate stage of the insertion of the transosseous suture assembly of the embodiment illustrated in FIGS. 1A-2B. As shown, the flexible and deformable sleeve 100, described in relation to FIGS. 1A-2B, becomes tightly engaged in the side bore 1302 of the bone after first being pulled into the side bore 1302 when first flexible thread 112 is pulled from outside top bore 1304, then having sleeve shortening thread 120 pulled from outside top bore 1304. Pulling sleeve shortening thread 120 causes distension of the middle section of the flexible and deformable sleeve 100 widening it and further engaging it in the bone. A plurality of lengths of suture 140 are seen to extend from both the side bore 1302 and the top bore 1304.

Figure 13A:
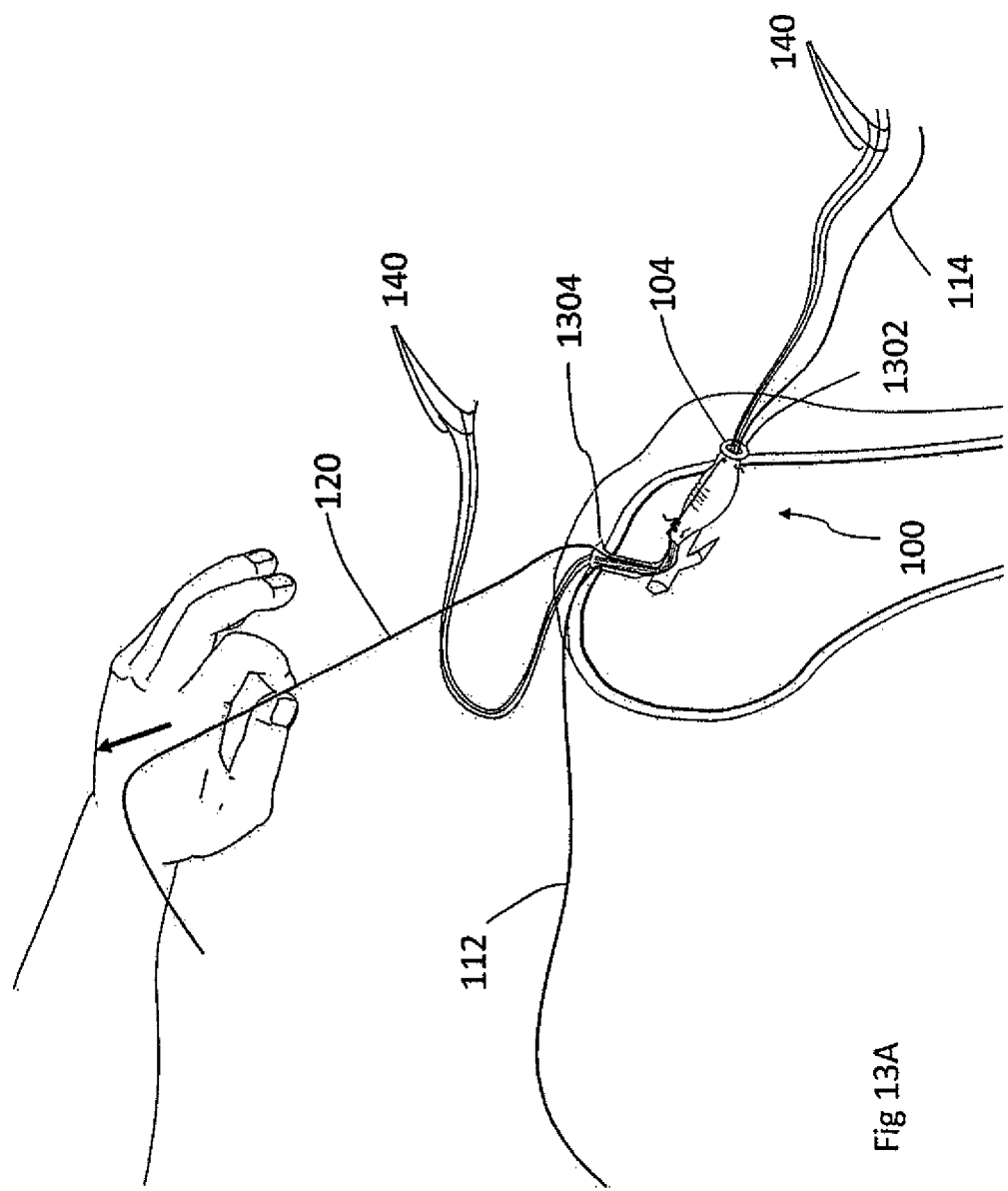
FIGS. 13A, 13B, 13C, 13D, 13E, 13F & 13G are simplified illustrations of the penultimate stage of the insertion of the transosseous suture assembly of various embodiments illustrated in FIGS. 1A-2B, FIGS. 3A-4B, FIGS. 5A-6B, FIGS. 7A & 7B, FIGS. 8A & 8B, FIGS. 9A & 9B, and FIGS. 10A-11B, respectively.
Figure 13B:
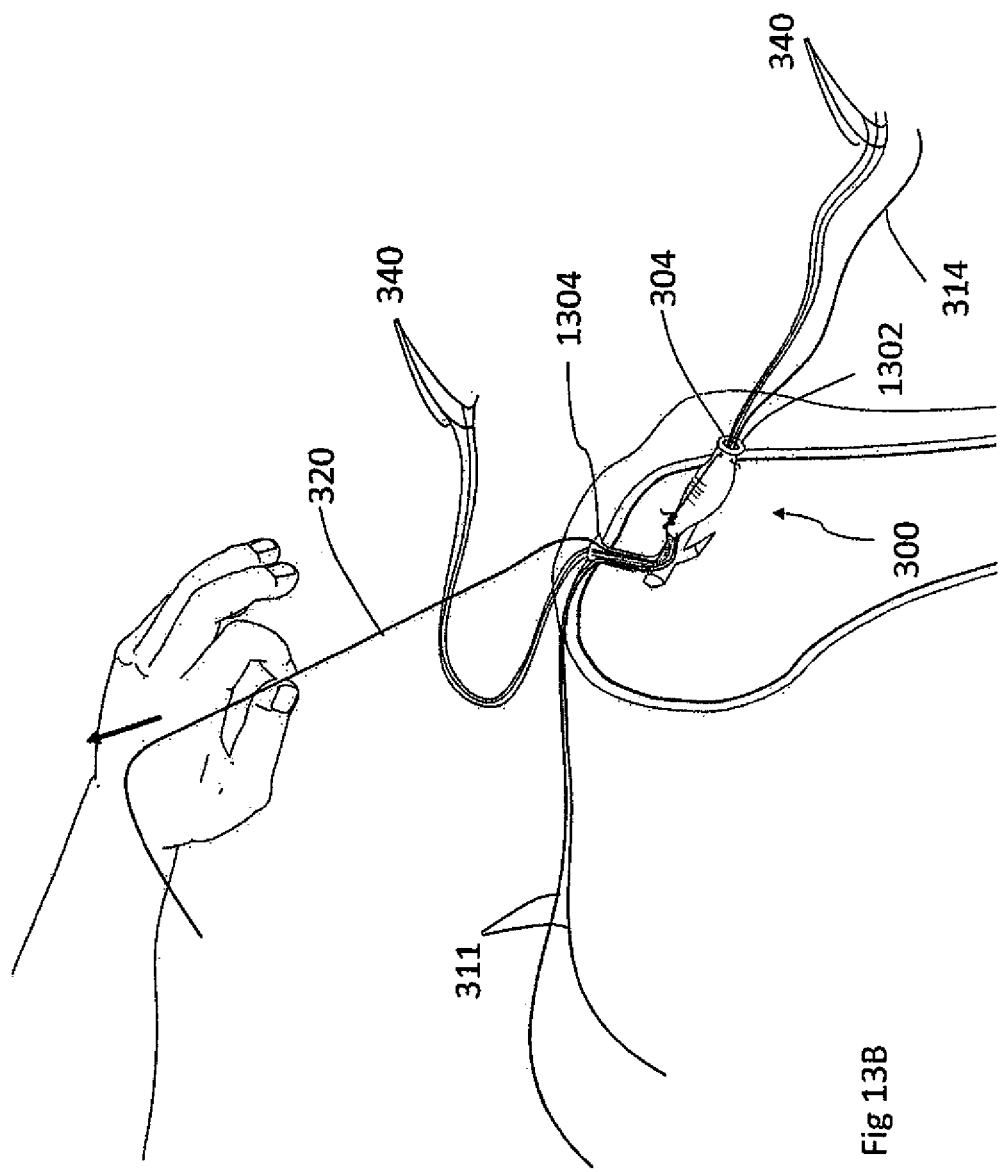

Reference is now made to FIG. 13B, which is a simplified sectional illustration of the penultimate stage of the insertion of the transosseous suture assembly of the embodiment illustrated in FIGS. 3A-4B. As shown, the flexible and deformable sleeve 300, described in relation to FIGS. 3A-4B, becomes tightly engaged in the side bore 1302 of the bone after first being pulled into the side bore 1302 when first flexible thread 311 is pulled from outside top bore 1304, then having tightening suture 320 pulled from outside top bore 1304. Pulling tightening suture 320 causes distension of the middle section of the flexible and deformable sleeve 300 widening it and further engaging it in the bone. Optionally, first flexible thread 311 may be pulled from top bore of bone by one of free ends 313 so that it is removed from flexible and deformable sleeve 300, once flexible and deformable sleeve 300 is fully engaged in side bore of bone. A plurality of lengths of suture 340 are seen to extend from both the side bore 1302 and the top bore 1304.

Figure 13C:
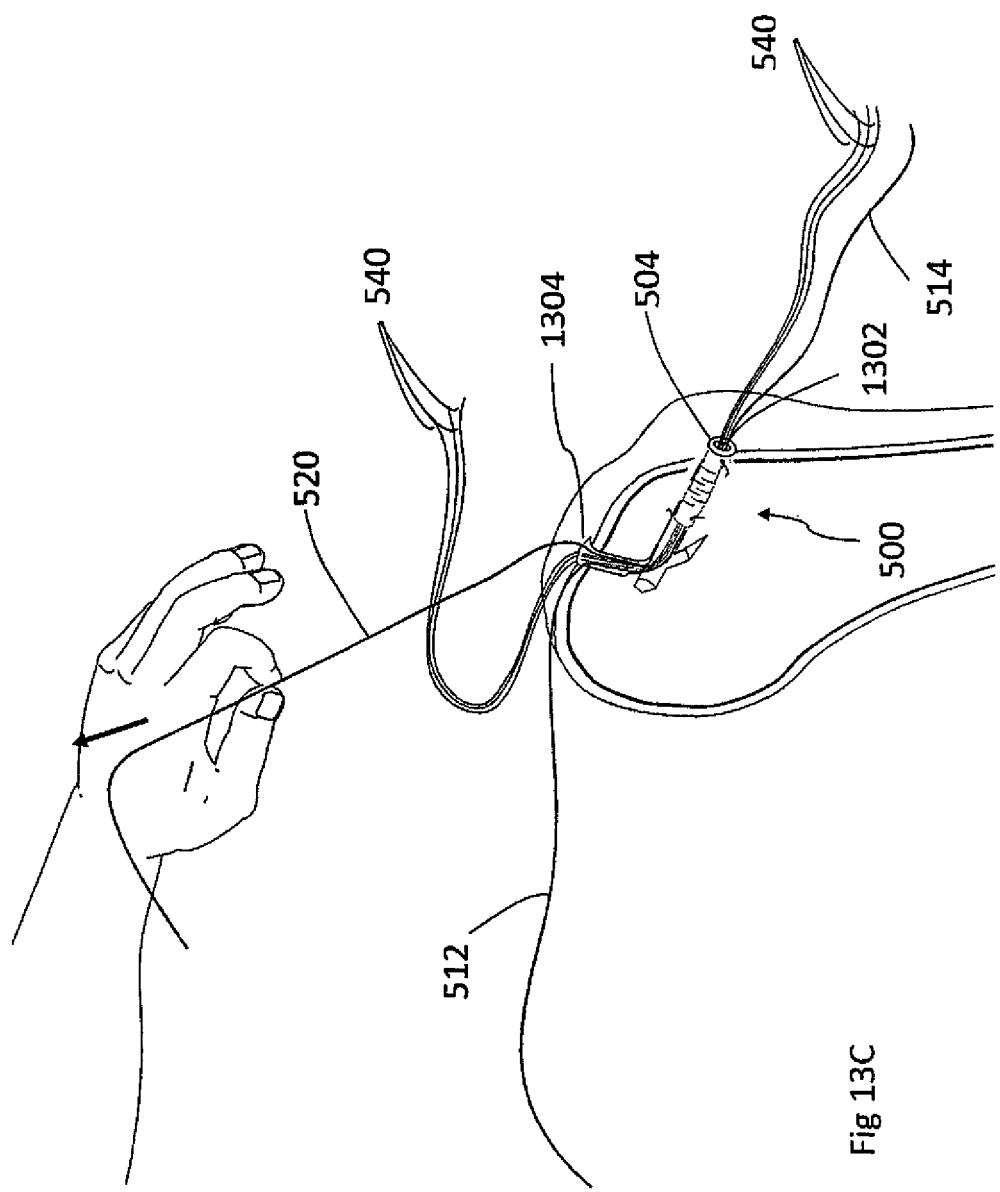

Reference is now made to FIG. 13C, which is a simplified sectional illustration of the penultimate stage of the insertion of the transosseous suture assembly of the embodiment illustrated in FIGS. 5A-6B. As shown, the flexible and deformable sleeve 500, described in relation to FIGS. 5A-6B and having an outer second sleeve 550, becomes tightly engaged in the side bore 1302 of the bone after first being pulled into the side bore 1302 when suture 512 is pulled from outside top bore 1304, then having sleeve shortening thread 520 pulled from outside top bore 1304. Pulling sleeve shortening thread 520 causes distension of the middle section of both the flexible and deformable sleeve 500 and the outer second sleeve 550, widening them and further engaging the flexible and deformable sleeve 500 in the bone. A plurality of lengths of suture 540 are seen to extend from both the side bore 1302 and the top bore 1304.

Figure 13D:
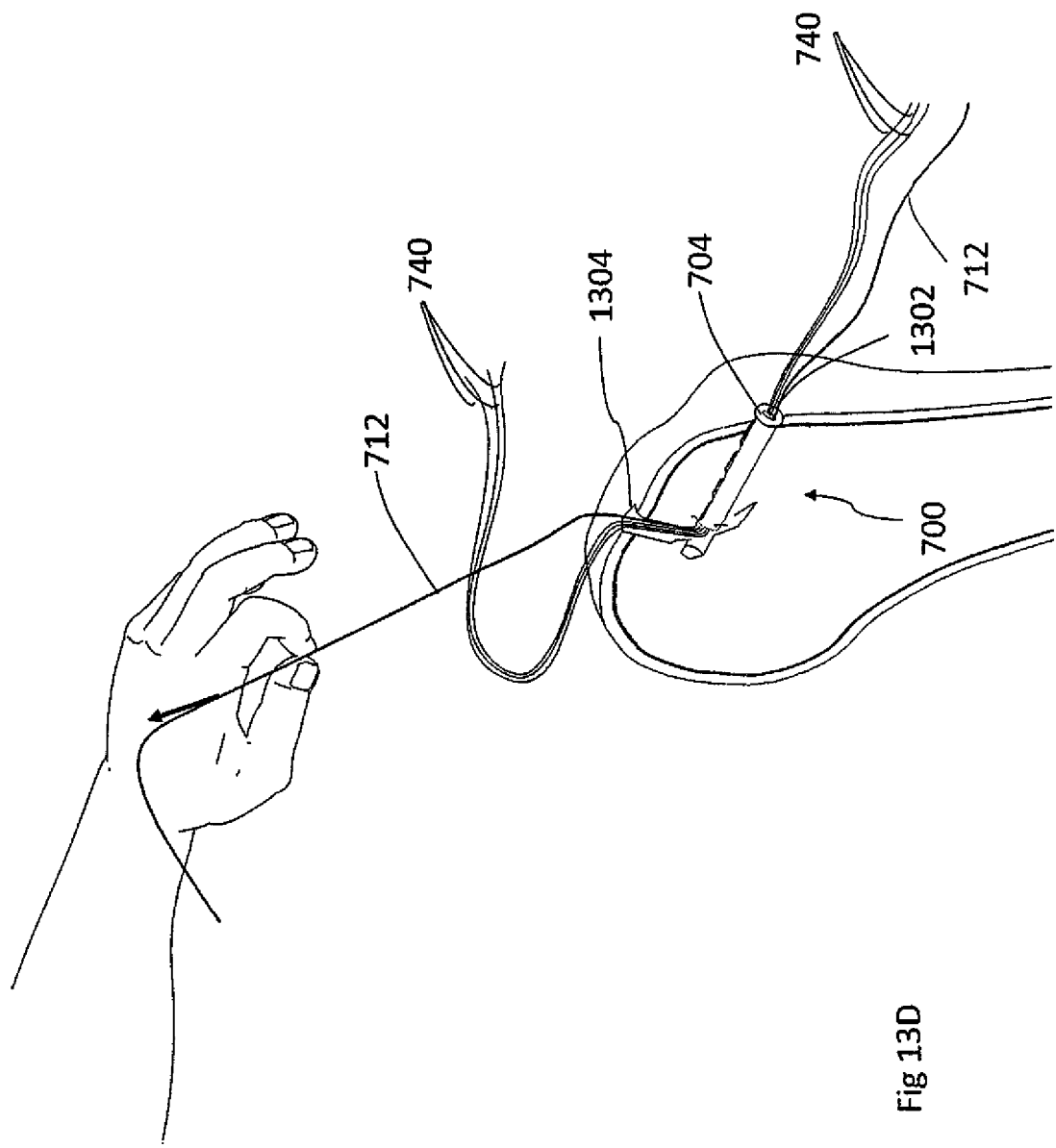

Reference is now made to FIG. 13D, which is a simplified sectional illustration of the penultimate stage of the insertion of the transosseous suture assembly of the embodiment illustrated in FIGS. 7A & 7B. As shown, the flexible sleeve 700, described in relation to FIGS. 7A & 7B, becomes engaged in the side bore 1302 of the bone after being pulled into the side bore 1302 when flexible thread 712 is pulled from outside top bore 1304. In other embodiments, a suture either fixed to, or looped through an aperture in sleeve is used to pull the sleeve into the bone. A plurality of lengths of suture 740 are seen to extend from both the side bore 1302 and the top bore 1304.

Figure 13E:
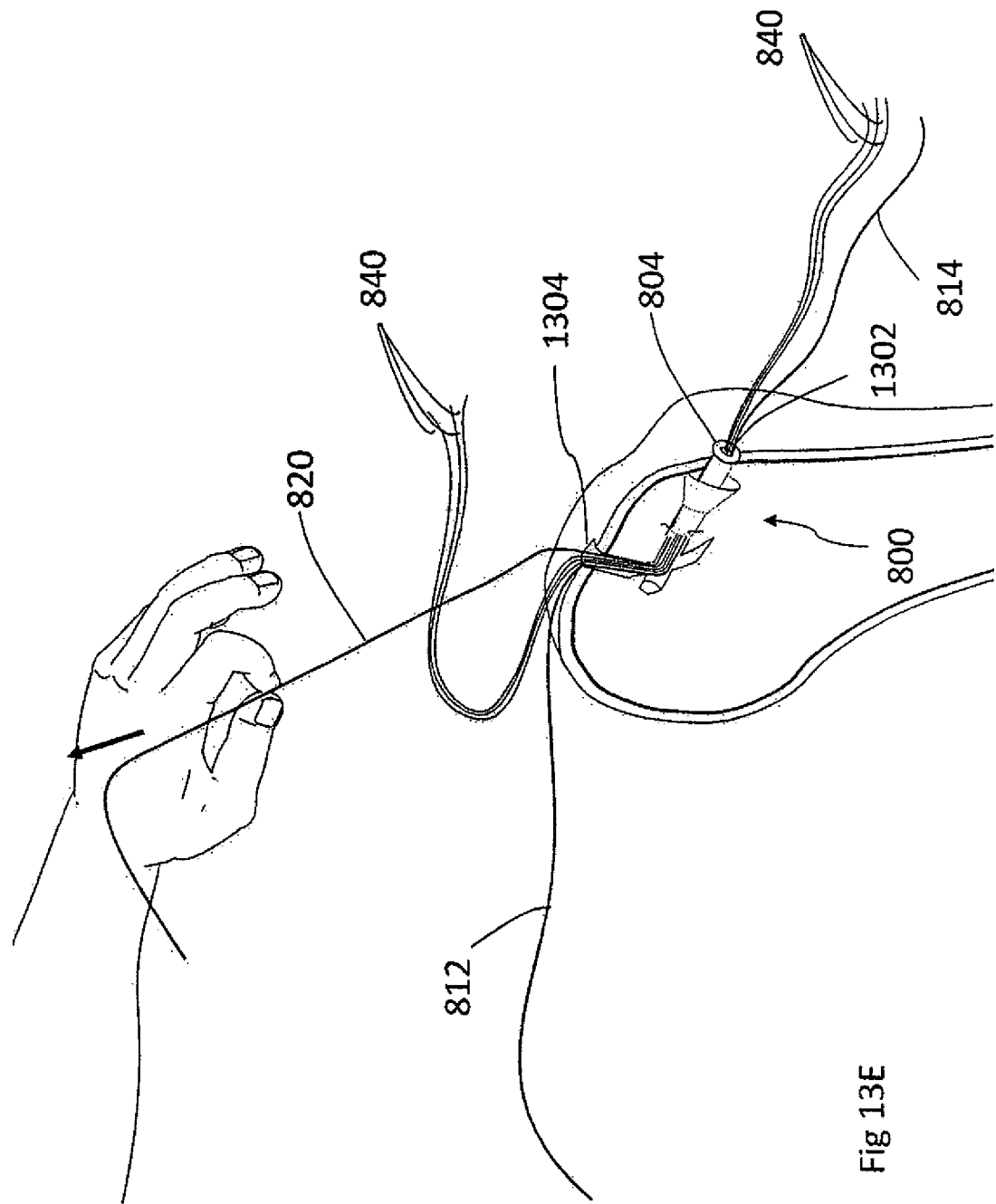
Figure 14:
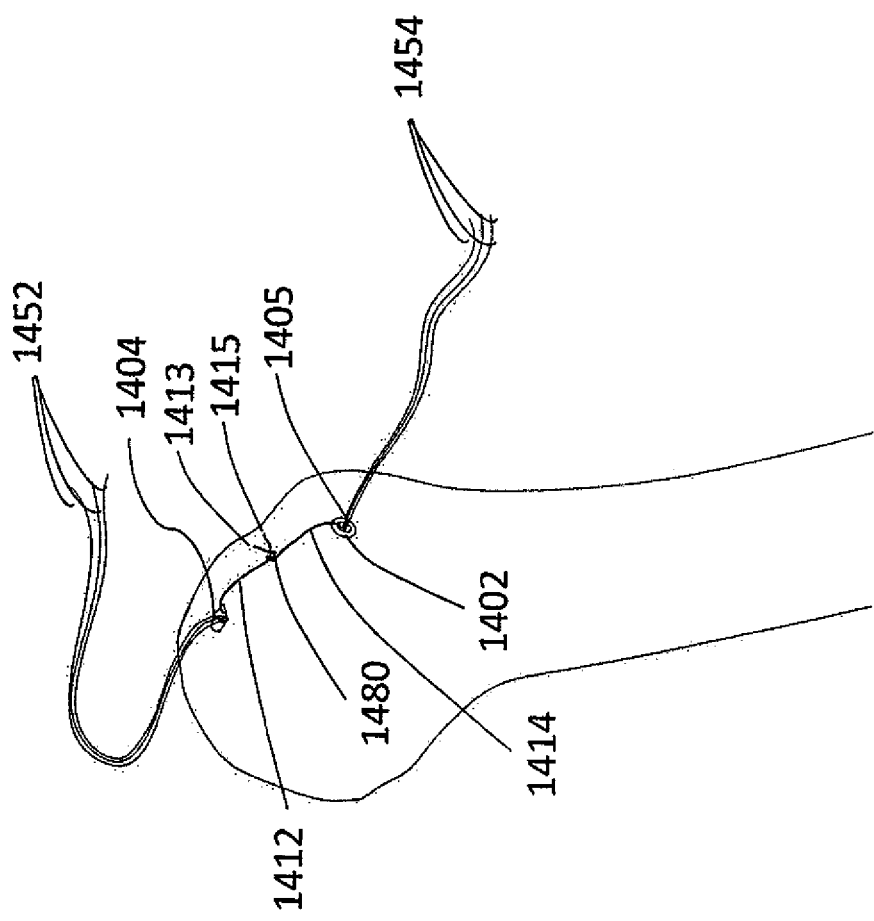
FIG. 14 is a simplified illustration of a final stage of the insertion of the transosseous suture assembly of all of the various embodiments illustrated in FIGS. 1A-11B.

Reference is now made to FIG. 13E, which is a simplified sectional illustration of the penultimate stage of the insertion of the transosseous suture assembly of the embodiment illustrated in FIGS. 8A & 8B. As shown, the flexible sleeve 800, described in relation to FIGS. 8A & 8B, becomes tightly engaged in the side bore 1302 of the bone after being pulled into the side bore 1302 when first flexible thread 812 is pulled from outside top bore 1304. When flexible sleeve 800 is pulled into bone, the flared outer second sleeve 850 flexes and its outer diameter is decreased as it passes into the side bore 1302. Once inside the osseous portion of the bone, the flared outer second sleeve recovers to near the original shape and, thus widened, causes tighter engagement in the bone. When optional tightening thread 820 is attached to flexible and deformable sleeve 800, it may be used to further tighten the engagement of the flexible sleeve in the bone by tying it together outside bone, similar to what is shown in FIG. 14 below. A plurality of lengths of suture 840 are seen to extend from both the side bore 1302 and the top bore 1304.

Figure 13F:
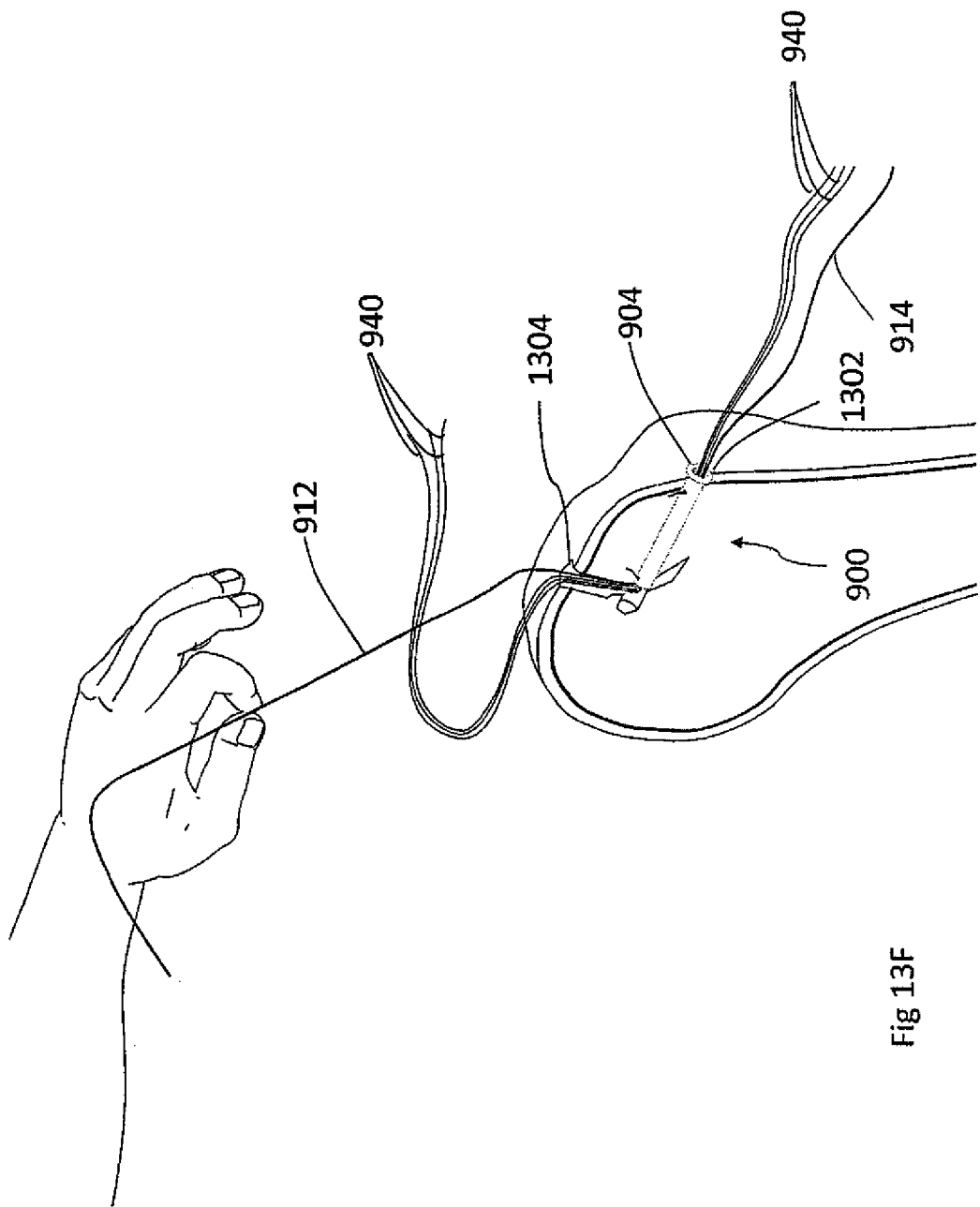

Reference is now made to FIG. 13F, which is a simplified sectional illustration of the penultimate stage of the insertion of the transosseous suture assembly of the embodiment illustrated in FIGS. 9A & 9B. As shown, the flexible sleeve 900, described in relation to FIGS. 9A & 9B, becomes engaged in the side bore 1302 of the bone after being pulled into the side bore 1302 when first flexible thread 912 is pulled from outside top bore 1304. A plurality of lengths of suture 940 are seen to extend from both the side bore 1302 and the top bore 1304.

Figure 13G:
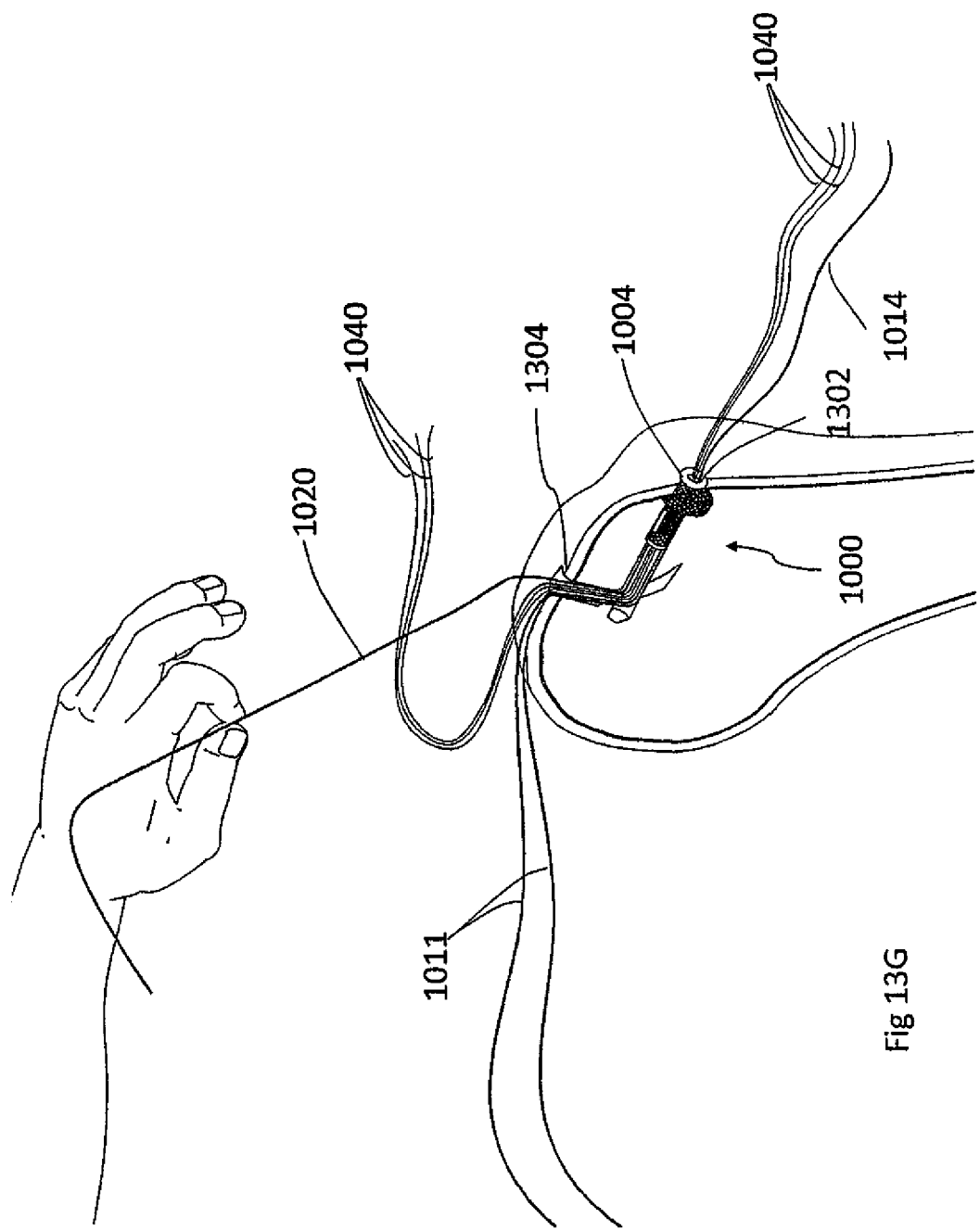

Reference is now made to FIG. 13G, which is a simplified sectional illustration of the penultimate stage of the insertion of the transosseous suture assembly of the embodiment illustrated in FIGS. 10A-11B. As shown, the flexible and deformable braided sleeve 1000, described in relation to FIGS. 10A-11B, becomes tightly engaged in the side bore 1302 of the bone after first being stretched then pulled into the side bore 1302 when first flexible thread 1011 is pulled from outside top bore 1304. The stretching causes the torus shaped portion 1050 of flexible and deformable braided sleeve 1000 to compress and the flexible and deformable braided sleeve 1000 to approximate a generally circular cylindrical shape, allowing passage of the flexible and deformable braided sleeve 1000 into the side bore 1302 of the bone. Upon entry into the osseous portion of the bone, and once tension caused by pulling on the first flexible thread 1011 is relaxed, the flexible and deformable braided sleeve 1000 relaxes and the pre-formed torus shaped portion 1050 reasserts itself, tightly engaging the flexible and deformable braided sleeve 1000 in the bone, as shown. Optionally, tightening thread 1020, when present, may tied together outside bone thus further tightening engagement of the transosseous suture in the bone. Optionally, first flexible thread 1011 may be pulled from top bore of bone by one of free ends 1013 so that it is removed from flexible and deformable sleeve 1000, once flexible and deformable braided sleeve 1000 is fully engaged in side bore of bone. A plurality of lengths of suture 1040 are seen to extend from both the side bore 1302 and the top bore 1304.

Alternatively, when the flexible and deformable braided sleeve 1000 has not been pre-stressed or pre-formed and flexible and deformable braided sleeve 1000 is generally circularly cylindrical in a relaxed state, the flexible and deformable braided sleeve 1000 becomes tightly engaged in the side bore 1302 of the bone after first being pulled into the side bore 1302 when first flexible thread 1011 is pulled from outside top bore 1304, then having tightening thread 1020 pulled from outside top bore 1304. Pulling tightening thread 1020 causes distension of the middle section of the flexible and deformable braided sleeve 1000 widening it and further engaging it in the bone. Optionally, first flexible thread 1011 may be pulled from top bore of bone by one of free ends 1013 so that it is removed from flexible and deformable sleeve 1000, once flexible and deformable sleeve 1000 is fully engaged in side bore of bone.

Reference is now made to FIG. 14, which is a simplified illustration of a final stage of the insertion of the transosseous suture assembly of each of the various embodiments illustrated in FIGS. 1A-11B. As shown, two loose ends 1413 and 1415 of sutures 1412 and 1414 attached to a sleeve now loosely engaged within the side bore 1402 in the bone, one extending through the top bore 1404 and one extending through the side bore 1402 respectively, are tied and knotted together tightly outside the bone, forming a knot 1480. This further engages the transosseous suture assembly within the bone. This final step is typically done for all embodiments of the current invention described above in FIGS. 1A-11B.

Applicants have realized that although the transosseous approach efficiently fixates a suture in the bone, padding the inner walls of the tunnel would be advantageous in protecting the bone.

Applicants have realized that passing a transosseous suture through a protective sleeve may protect the bone and may also assist in fixating the suture within the transosseous tunnel, preventing its movement and subsequent displacement from within the tunnel during deployment and thereafter.

Figure 15B:
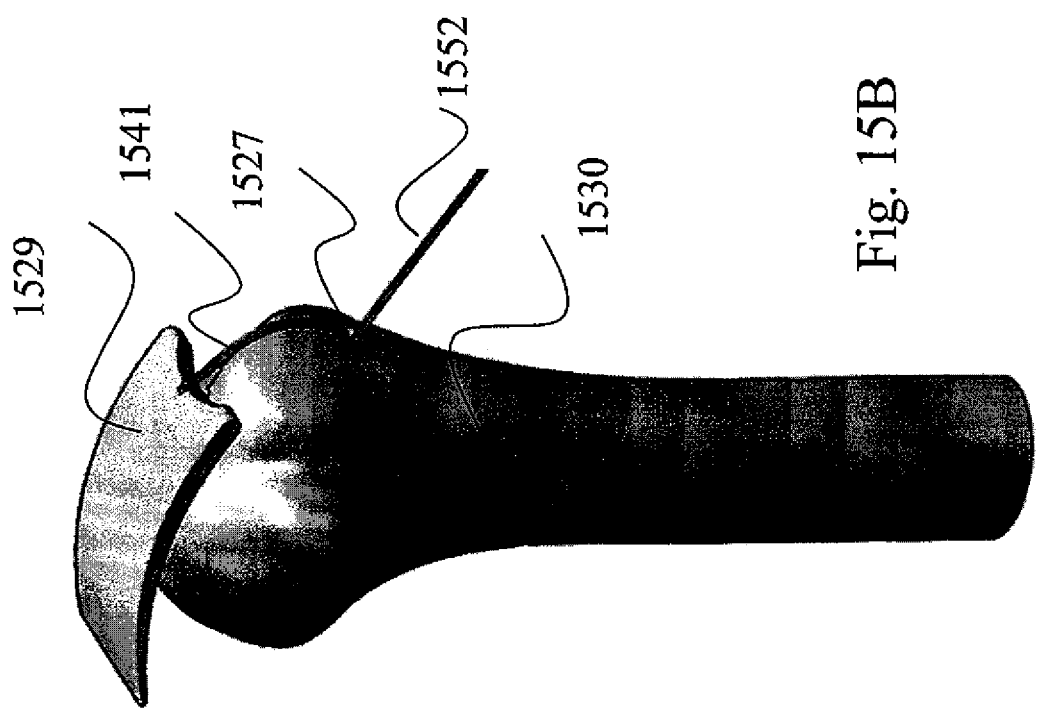
FIGS. 15A and 15B are schematic illustrations of a padded transosseous suture configuration, in cross-section and in solid, where the suture is passed through a protective fixation sleeve, constructed and operative in accordance with yet a further embodiment of the present invention, in situ.
Figure 15A:
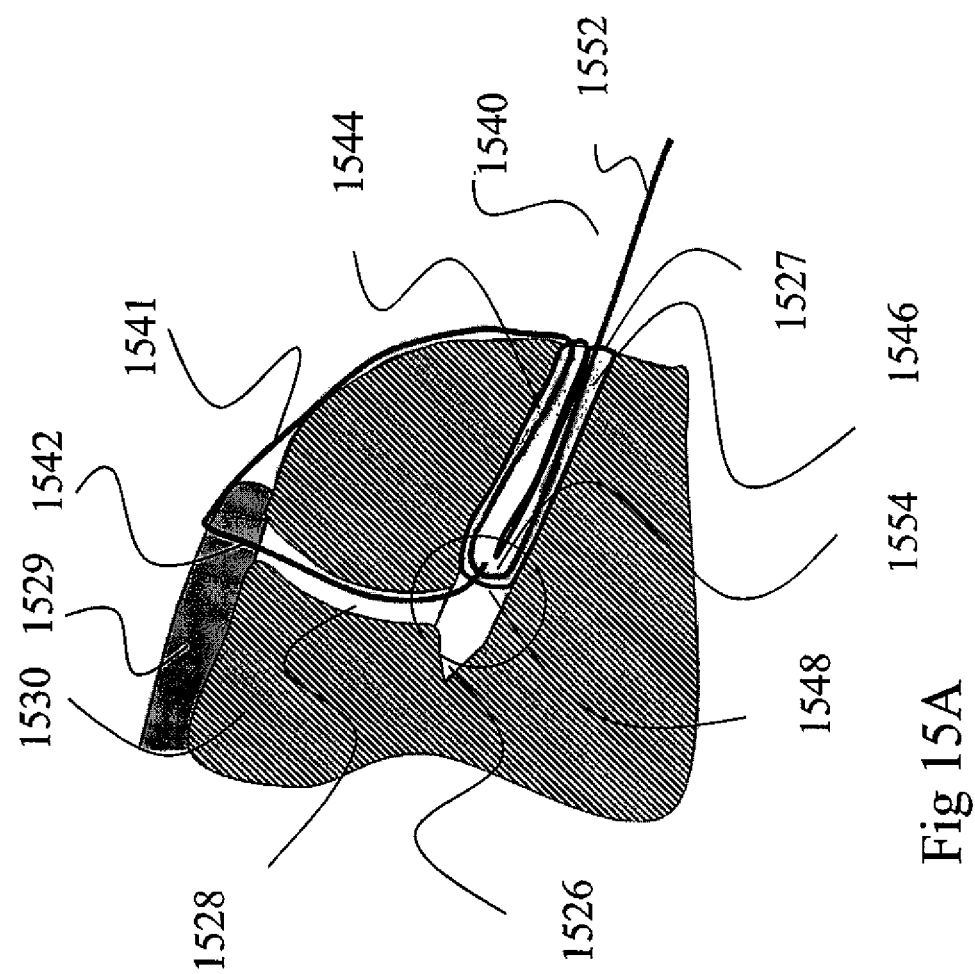

Reference is now made to FIG. 15A, which illustrates a padded transosseous suture (PTS) 1540, constructed and operative in accordance with a preferred embodiment of the present invention, and shown in situ after PTS 1540 has been implanted in bone 1530. PTS 1540 may comprise a suture 1541, seen in the side view of FIG. 15A, and a padding 1546. Suture 1541 may be divided, generally into three segments, a tunnel segment 1542, a padded segment 1544 and an extending section 1552, where padding 1546 around a portion of padded segment 1544. Tunnel segment 1542 may connect to a rear section 1548 of padding 1546 and may extend, when in situ, from the back of first tunnel 1526 up through tunnel 1528 and through tendon 1529. It may continue on top of tendon 1529 to padding segment 1544.

When in situ, padding 1546 may be folded inside of first tunnel 1526. Padding segment 1544 may extend into first tunnel 1526 where it may pass through padding 1546 and thus, may also be folded. It may extend back out of tunnel 1526, becoming extending segment, labeled 1552, which may also be used to tie off suture 1541.

Reference is now briefly made to FIG. 15B which is an isometric solid drawing of PTS 1540 after implantation. Suture 1541 can be seen going through tendon 1529 to bring it in contact with the bone 1530, with extending segment 1552 extending from first tunnel 1526. As shown hereinbelow in FIG. 16A, suture 1541 may be threaded through or otherwise connected to padding 1546, thereby to provide two of each suture segment. Thus, the two extending segments 1552 may be tied together in a knot at the opening 1527 of first tunnel 1526 once padding 1546 is in place. This will prevent suture 1541 from moving in the tunnels and will keep tendon 1529 in place.

Applicants have realized that an unpressed fold in a fabric generally is an area where the fabric is thick. Thus, the area of the fold, labeled 1554, may be an area of greater friction and may serve to hold PTS 1540 in place in first tunnel 1526. Thus, padding 1546 may be sized such that, at fold 1554, padding 1546 may push against first tunnel 1526. Moreover, since second tunnel 1528 may be at an angle, such as between 40 and 170 degrees, with first tunnel 1526, padding 1546 may not move into second tunnel 1528.

It will be appreciated that padding 1546 may both hold PTS 1540 in situ and may pad padded segment 1544 to keep it from rubbing against the inner surface of first tunnel 1526. Moreover, due to the connection of tunnel segment 1542 at the back of fold 1554, tunnel segment 1542 may be held largely in the middle of second tunnel 1528 and thus, may also not rub against the inner surface of second tunnel 1528.

It will also be appreciated that PTS 1540 may be self-locking inside tunnel 1528 due to the friction against fold 1554. Accordingly, PTS 1540 will generally not move from its final position.

PTS 1540 may be placed into tunnels 1526 and 1528 by pulling tunnel segment 1542 (which may already be in the tunnels, as described in more detail hereinbelow) from the entrance of first tunnel 1526 towards second tunnel 1528. Since tunnel segment 1542 may be connected to rear segment 1548, it may force padding 1546 to fold in order to enter first tunnel 1528. Pulling tunnel segment 1542 further may pull padding 1546 into first tunnel 1528.

Figures 16A, 16B:
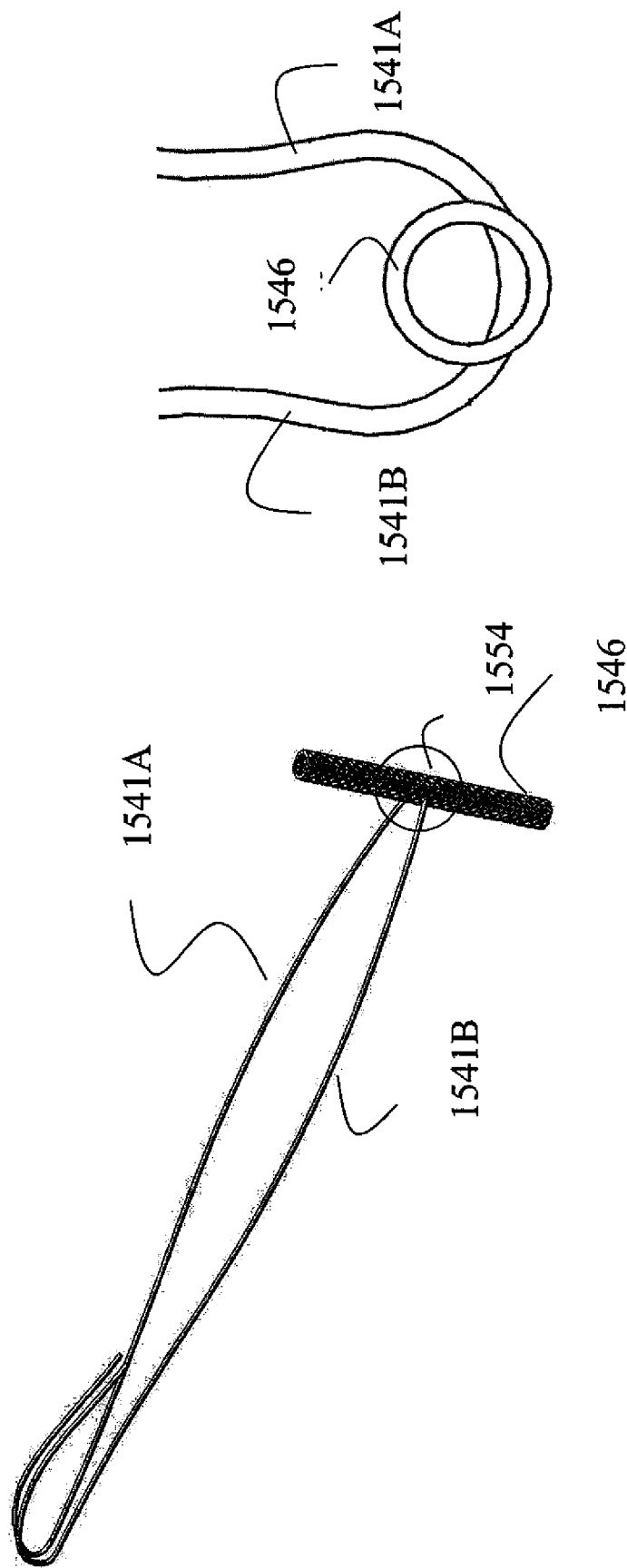
FIGS. 16A & 16B are schematic and cross-sectional illustrations, respectively, of a protective fixation sleeve and a suture passed through a cross section of the sleeve, prior to implantation.

Reference is now made to FIGS. 16A and 16B, which illustrates PTS 1540 before it is implanted in the bone and shows suture 1541 passing through padding 1546, thereby to connect suture 1541 to padding 1546. As a result of passing through or otherwise being connected to padding 1546, suture 1541 may have two strings, labeled 1541A and 1541B, enabling the two ends of suture 1541 to be easily tied.

As can be seen in FIG. 16B, padding 1546 may be of a cylindrical shape and suture 1541 may pass through any appropriate section of its interior. Moreover, suture 1541 may generally be connected at midpoint 1554 of padding 1546.

In an alternative embodiment, strings 1541A and 1541B may be separately connected to padding 1546 or they may be formed from a doubling over of suture 1541.

Padding 1546 may be formed of any suitable material which may be bio-compatible and may be flexible enough to fold and through which suture 1541 may be threaded and pulled. For example, as shown in FIG. 16A, padding 1546 may be a generally cylindrical shape made of a braided material and/or may be made with a braid similar to that of a shoestring. Alternatively, padding 1546 may be formed from a bio-compatible silicone or plastic. Furthermore, padding 1546 may be any suitable bio-compatible material which may be flexible and foldable, and through which suture 1541 may be threaded, as described hereinbelow.

Figure 16D:
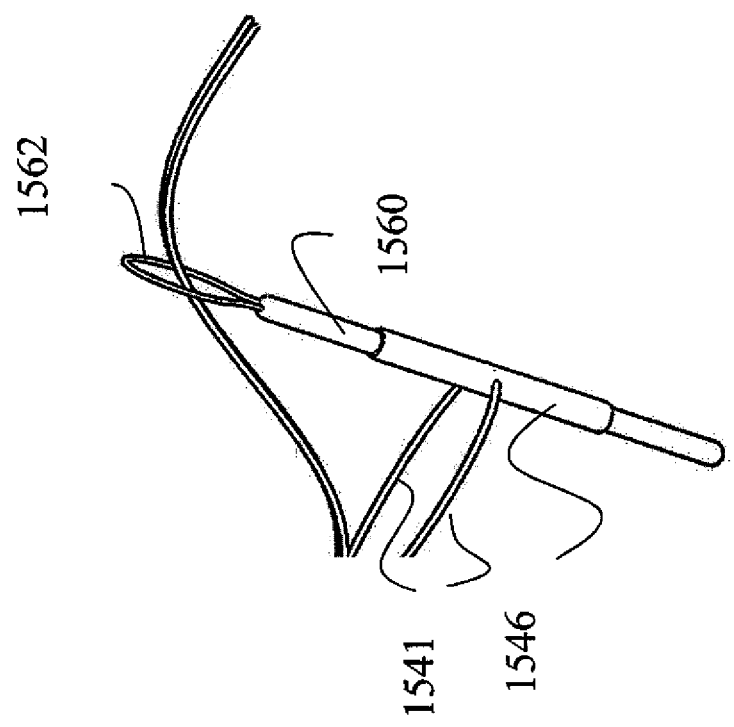
FIG. 16D is a schematic illustration of the sleeve and suture of FIG. 16A with the threader of FIG. 16C passed through the sleeve, prior to implantation.
Figure 16C:
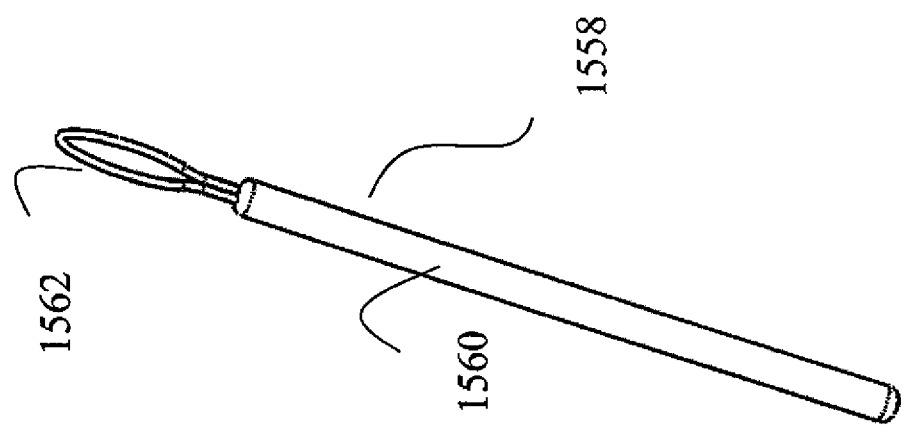
FIG. 16C is a schematic illustration of a threader for the suture of FIG. 16A.

Reference is now made to FIGS. 16C and 16D, which illustrate a threader 1558 useful in threading PTS 1540. As shown in FIG. 16C, threader 1558 may comprise a handle 1560 and a threading loop 1562, typically made of any suitable, thin, flexible wire. Prior to implantation and/or during manufacture, handle 1560 may be threaded through padding 1546, with threading loop 1562 left external to padding 1546. As shown in FIG. 16D, suture 1541 may be threaded through loop 1562 prior to its being pulled through padding 1546 during the implantation process, thereby threading both strings of suture 1541 through padding 1546.

Reference is now made to FIGS. 17A-17K, which illustrate the process of implanting PTS 1540 into bone 1530.

FIGS. 17A-17K generally show the bone in a side view and thus, for clarity, do not always show both strings of suture 1541.

Figure 17A:
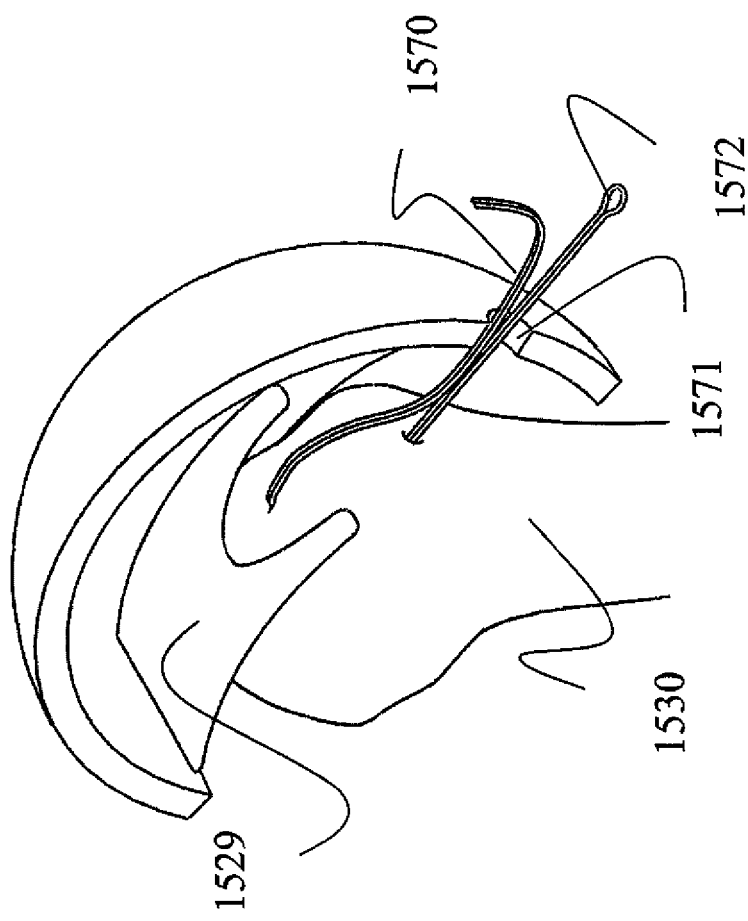
FIGS. 17A, 17B, 17C, 17D, 17E, 17F, 17G, 17H, 17I, 17J and 17K are schematic illustrations of the process of implanting the padded transosseous suture of FIGS. 16A-16D.

FIG. 17A shows bone 1530 after creating transosseous tunnels 1526 and 1528. The transosseous process leaves a wire shuttle 1570 threaded through tunnels 1526 and 1528, and through a cut 1571 in the skin. Note that tendon 1529 is not yet connected to bone 1530.

Figures 17B, 17C:
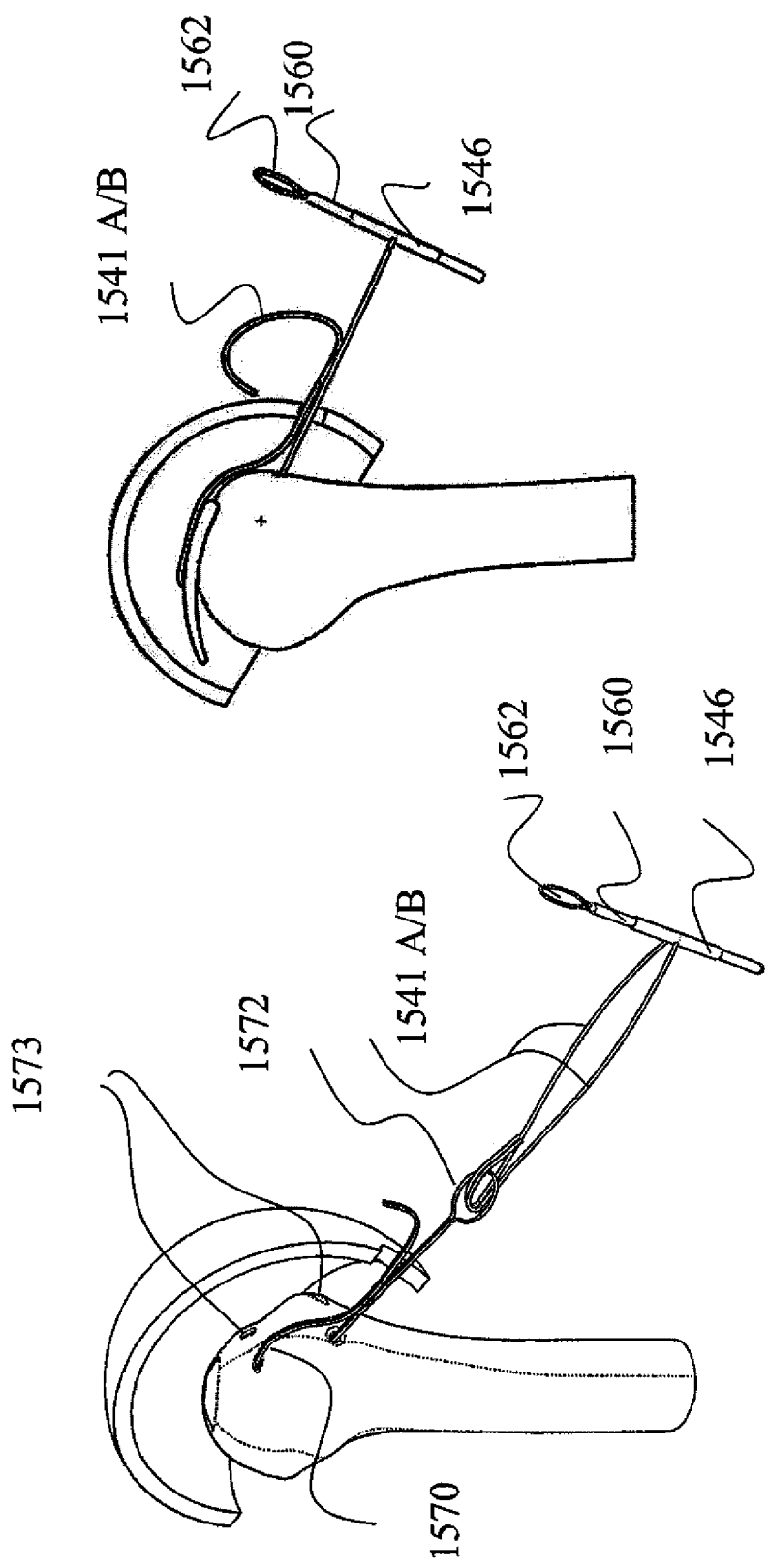
Figure 17E:
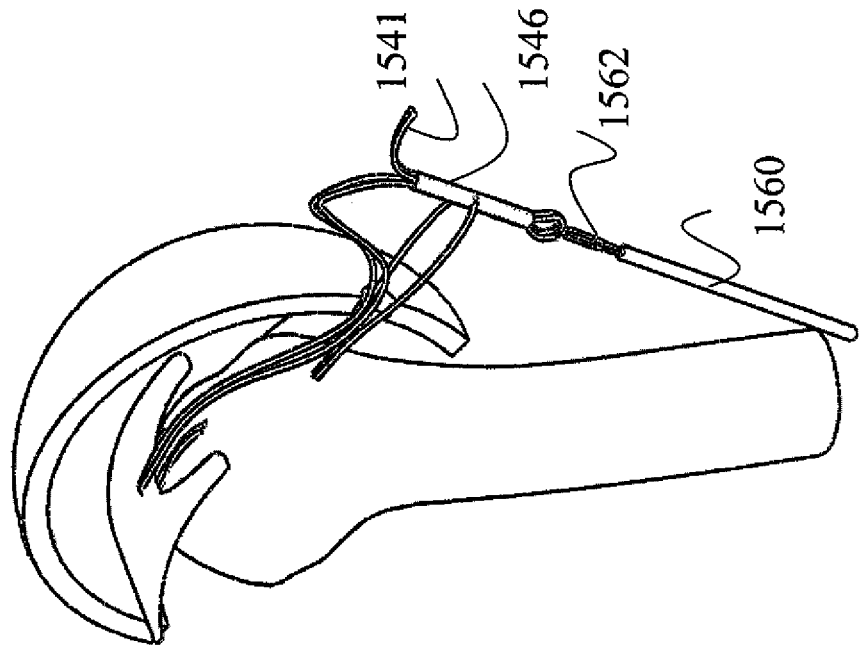

Shuttle 1570 has a loop 1572 into which a surgeon may thread strings 1541A and 1541B of suture 1541, as shown in FIG. 17B. At this stage, handle 1560 is still held within padding 1546. FIG. 17B also shows a second set of exit holes 1573 for the second PTS 1540 so that a surgeon may tie a criss-cross stitch. The remaining discussion will show the process on only one PTS 1540.

The surgeon may pull wire shuttle 1570 through bone 1530, thereby replacing wire shuttle 1570 with suture 1541. Using appropriate surgical tools, such as suture passers, the surgeon may then pass suture 1541 through tendon 1529 and back out of the body through cut 1571. The result is shown in FIG. 17C.

Typically a tendon to be repaired will have non-straight edge. The surgeon may pass suture 1541 through a point 1545 some distance behind the tear. During the process described hereinbelow, this point may be pulled forward towards the opening of the transosseous tunnel.

Figure 17D:
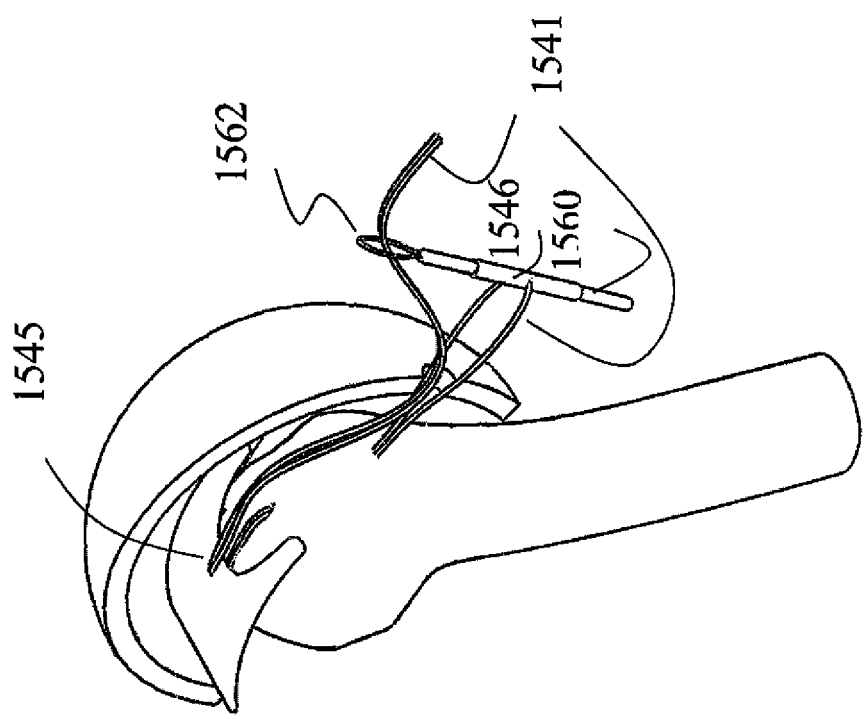

Outside of the body, the surgeon may now thread suture 1541 through wire loop 1562 of handle 1560, as shown in FIG. 17D. Pulling handle 1560 (FIG. 17E) may pull suture 1541 through padding 1546, thereby creating a loop from suture 1541, which is now looped through padding 1546.

Figure 17F:
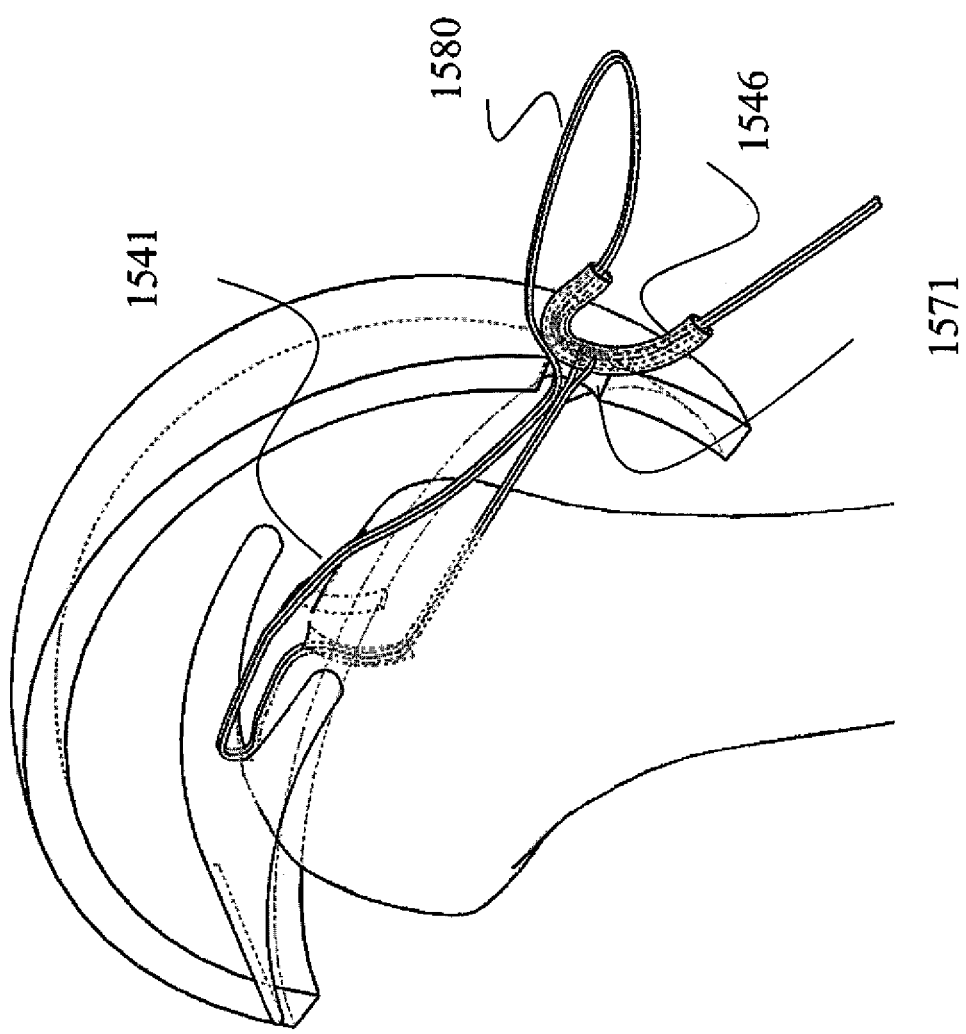
Figure 17G:
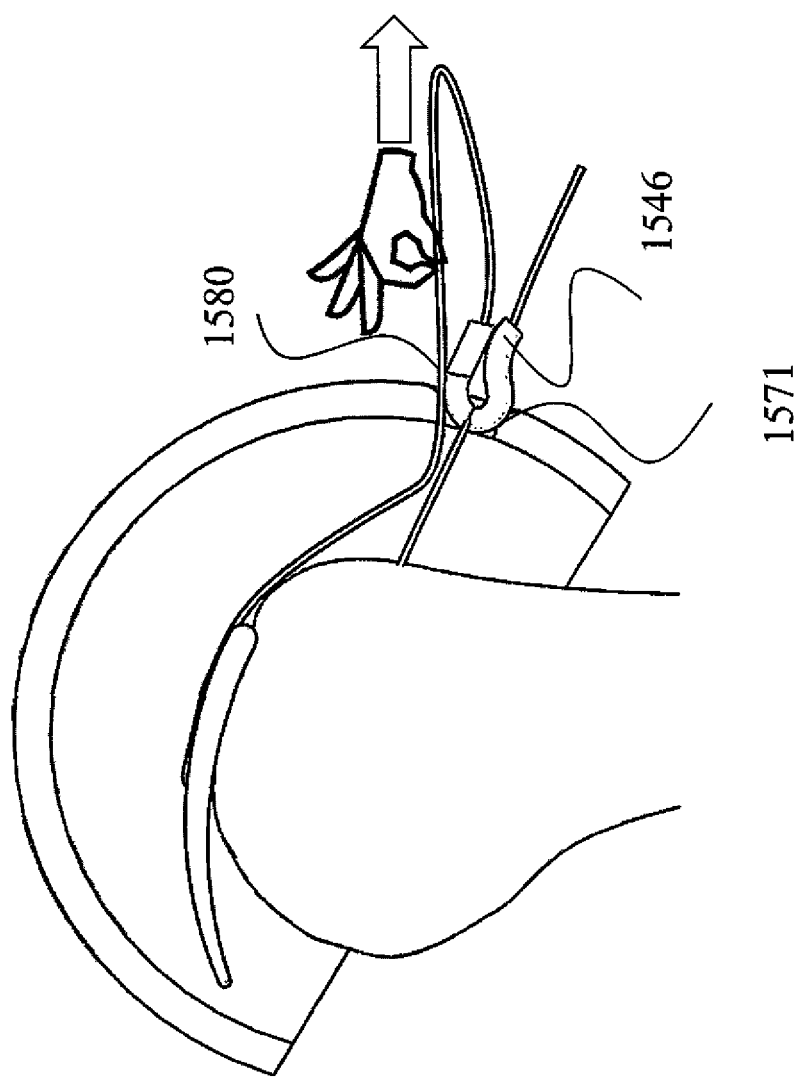
Figure 17H:
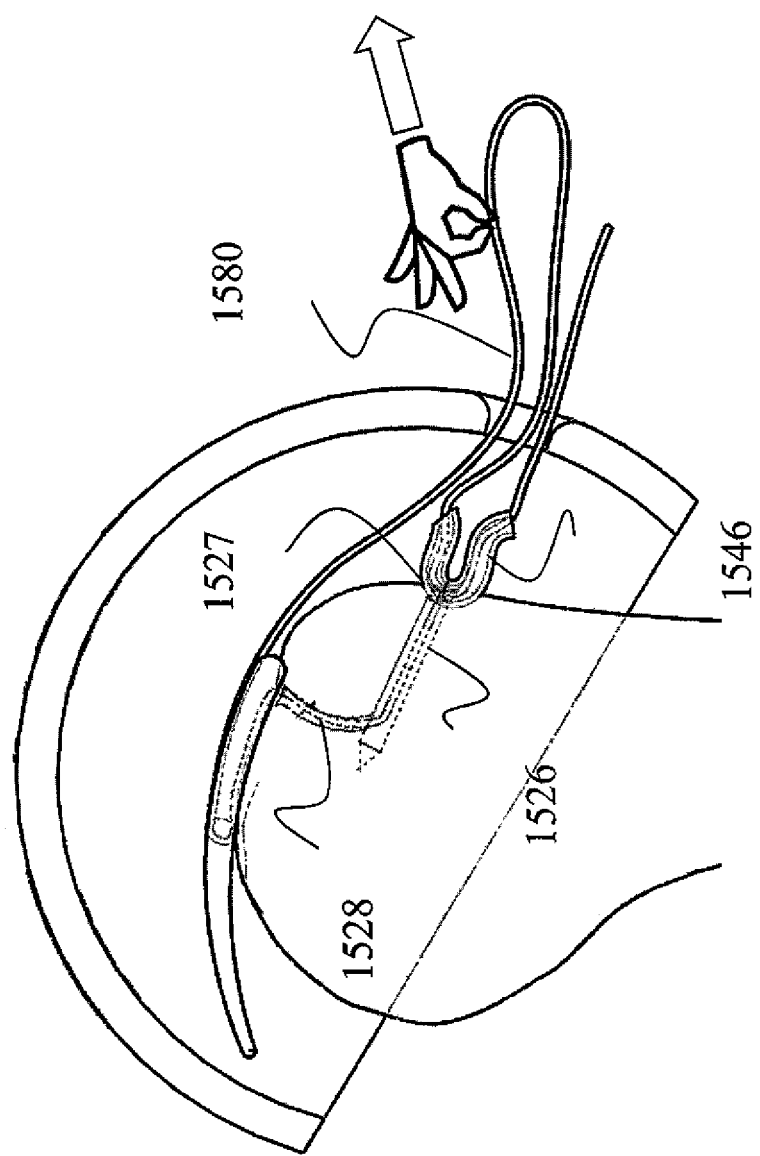

Due to the threading of suture 1541 within padding 1546, continued pulling on the portion 1580 of suture 1541, which is outside of the body and not past padding 1546, may bring padding 1546 towards cut 1571 in the skin (FIG. 17F). As shown in FIG. 17G, further pulling on portion 1580 may cause padding 1546 to bend, due to the connection of suture 1541 to generally the middle of padding 1546, as padding 1546 is pulled through cut 1571. Still further pulling on portion 1580 may pull bent padding 1546 towards and into opening 1527 of first tunnel 1526 (FIG. 17H).

Figure 17I:
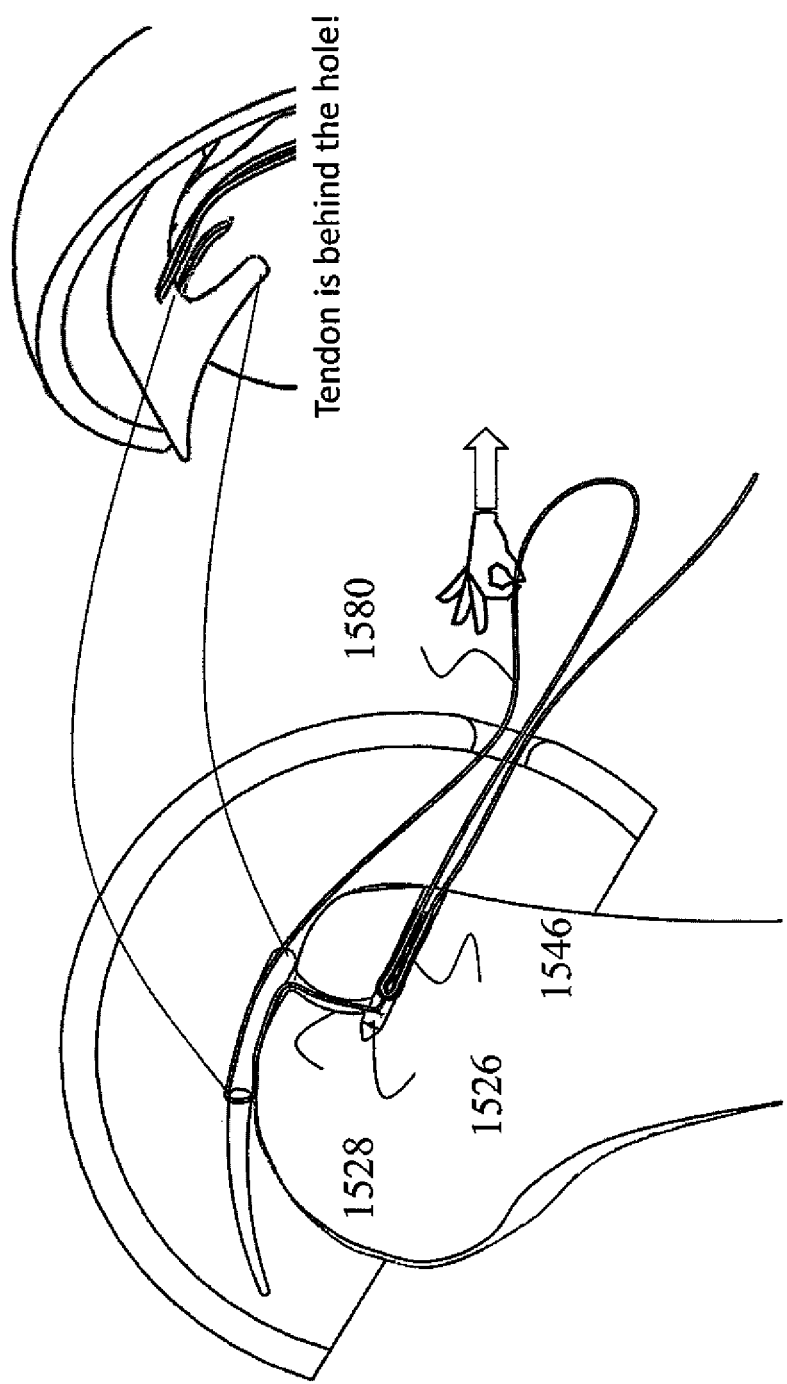
Figure 17J:
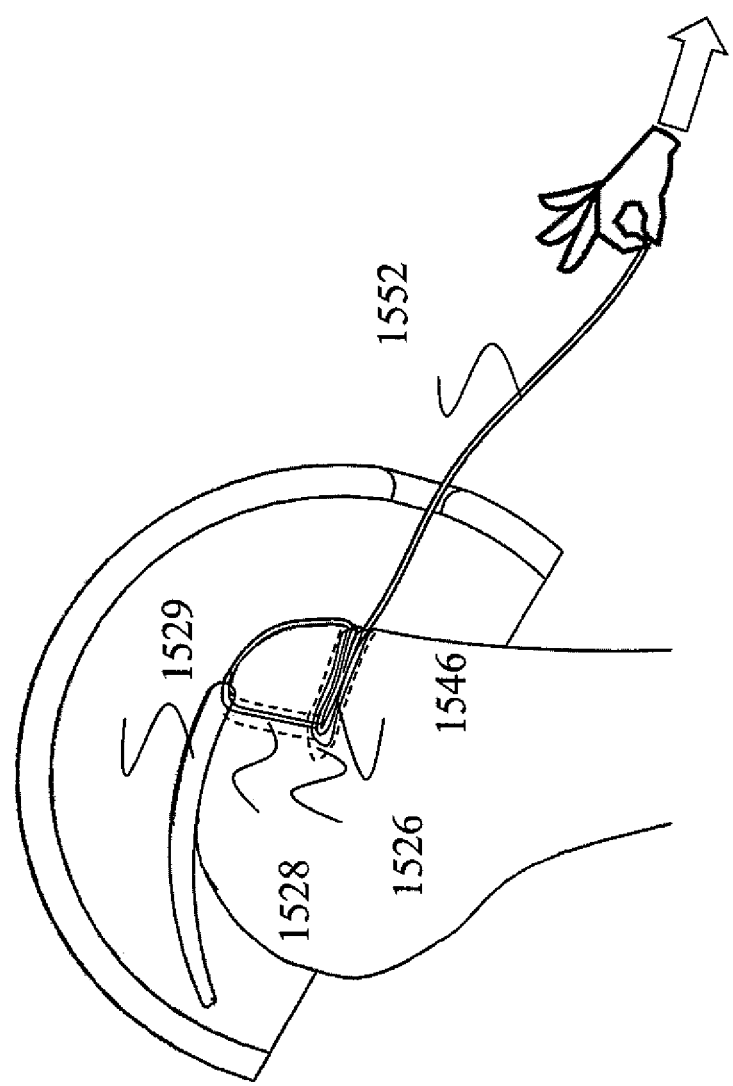
Figure 17K:
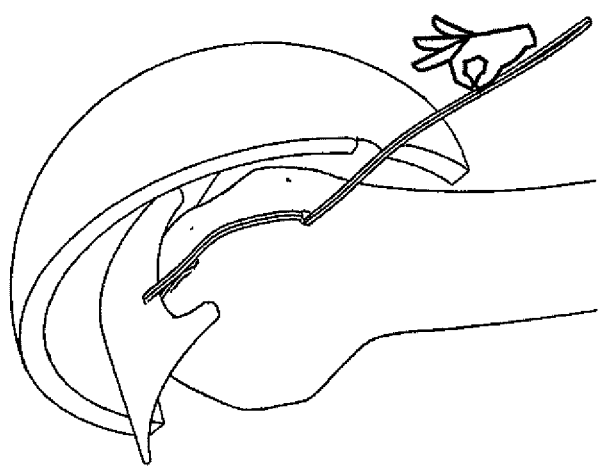

Continued pulling on portion 1580 will fold padding 1546 and bring it fully into first tunnel 1526 (FIG. 17I). The surgeon may pull padding 1546 through tunnel 1526 until padding 1546 stops. This may be at any point within tunnel 1526 but it will not extend beyond the intersection of the first tunnel and the second tunnel 1528 where the angle would require applying additional force to be applied in order to overcome the friction and resistance of moving around the angle of the turn. At this point, with padding 1546 fixed in place, suture 1541 may be tightened. There are two steps to this:

1) Pulling on extending segment 1552, exiting first tunnel 1528. This will pull suture 1541 through padding 1546 such that suture 1541 will lie tightly on the bone, as shown in FIG. 17J; and 2) Still further pulling on extending segment 1552, until it cannot be pulled any more. This will stretch tendon 1529 and bring it to its place over second tunnel 1528, as shown in FIG. 17K.

Finally, with suture 1541 tightly fastened and tendon 1529 in place, extending segment 1552 of suture 1541 may be tied together (recall that there are two of them) in a knot over cut 1571, in a criss-cross knot, a button closure or with any other suitable closure. After this, suture 1541 may be cut.

It will be appreciated that suture 1541 may be fixed due to frictions in tunnel 1526, from padding against the walls of tunnel 1526 but also from the fact that padding 1546 is folded. Moreover, pulling on the portions of suture 1541 external to the skin may pull on fold 1554 of padding 1546, which, in turn, may pull on padding segments 1544, which are connected to the external pulled portions.

It will be appreciated that, at any time during the process, padding 1546 may be pulled out of the joint, by pulling backwards on segment 1580 or on extending segment 1552. Similarly, padding 1546 may be pulled out after cutting suture 1541.

It will be appreciated that, by pulling padding 1546 from behind and through a thin opening, padding 1546 may be forced to bend, which creates a strong friction connection to first tunnel 1526 in the bone.

Figure 18:
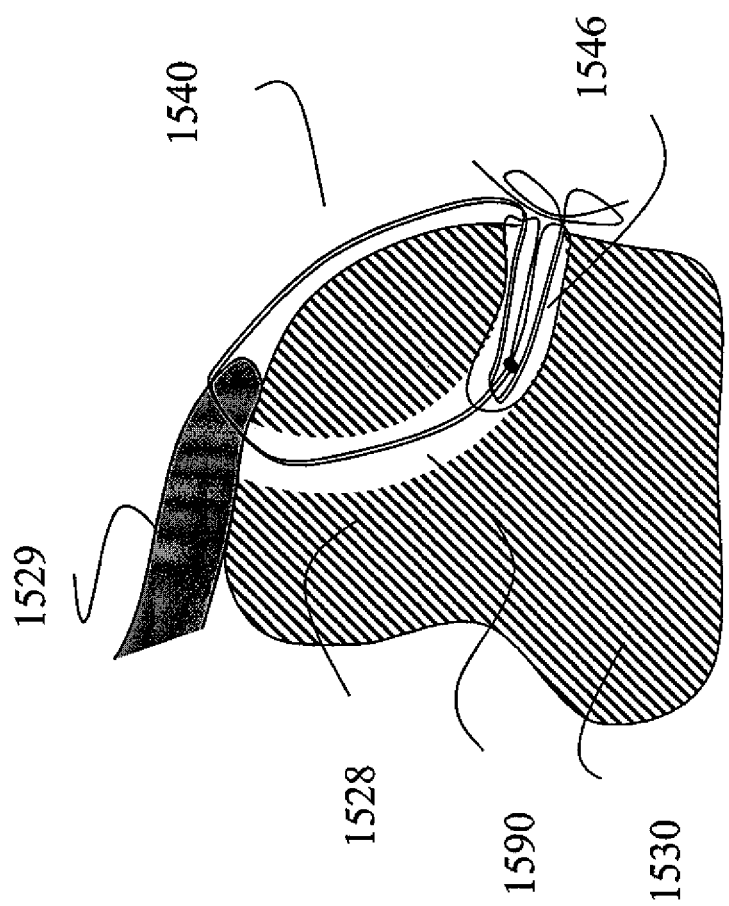
FIG. 18 is a schematic illustration of an alternative embodiment of the present invention.

It will be appreciated that the present invention may be utilized with any suitable transosseous tunnel(s). For example and as shown in FIG. 18, to which reference is now made, PTS 1540 may be threaded through a circular tunnel 1590 rather than through two tunnels 1526 and 1528.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A bone suture assembly comprising:
   a flexible generally cylindrical sleeve;
   a plurality of lengths of suture extending through said generally cylindrical sleeve;
   at least one sleeve securing thread associated with said generally cylindrical sleeve; and
   a flexible outer sleeve,
   at least a portion of said flexible outer sleeve overlying at least a portion of said flexible generally cylindrical sleeve,
   said plurality of lengths of suture extending through said flexible outer sleeve,
   said flexible outer sleeve comprising a cylindrical portion and a conical portion;
   said cylindrical portion having a diameter approximately matching that of an exterior of the generally cylindrical sleeve; and
   said conical portion extending outwardly of said generally cylindrical sleeve.

2. A bone suture assembly according to claim 1, wherein said generally cylindrical sleeve is deformable.

3. A bone suture assembly according to claim 2, further comprising at least one thread associated with said deformable cylindrical sleeve for selectively deforming said generally cylindrical sleeve.

4. A bone suture assembly according to claim 3, wherein said at least one thread for selective deforming comprises a thread which is looped through apertures at opposite ends of said generally cylindrical sleeve and when pulled, draws said opposite ends towards each other, thereby deforming said generally cylindrical sleeve.

5. A bone suture assembly according to claim 1, wherein said generally cylindrical sleeve comprises a flange formed at one end of said generally cylindrical sleeve.

6. A bone suture assembly according to claim 1, wherein said at least one sleeve securing thread includes at least one thread attached to said generally cylindrical sleeve at an end of said generally cylindrical sleeve.

7. A bone suture assembly according to claim 1, wherein said at least one sleeve securing thread includes at least one thread looped through an aperture formed in said generally cylindrical sleeve at an end of said generally cylindrical sleeve.

8. A bone suture assembly according to claim 1, wherein said at least one sleeve securing thread includes at least one thread stitched along said generally cylindrical sleeve and having free ends extending beyond ends of said generally cylindrical sleeve.

\* \* \* \* \*